(12) United States Patent
Moore et al.

(10) Patent No.: US 12,075,322 B2
(45) Date of Patent: Aug. 27, 2024

(54) SHORT RANGE PEER TO PEER NETWORK FOR NEGATIVE PRESSURE WOUND THERAPY DEVICES

(71) Applicant: KCI LICENSING, INC., San Antonio, TX (US)

(72) Inventors: Brett L. Moore, San Antonio, TX (US); Justin Rice, San Antonio, TX (US); Edward Lee, San Antonio, TX (US); Christian Romero, San Antonio, TX (US); Shannon C. Ingram, Bulverde, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 496 days.

(21) Appl. No.: 16/667,059

(22) Filed: Oct. 29, 2019

(65) Prior Publication Data

US 2020/0129674 A1 Apr. 30, 2020

Related U.S. Application Data

(60) Provisional application No. 62/753,759, filed on Oct. 31, 2018.

(51) Int. Cl.
*H04W 4/80* (2018.01)
*A61M 1/00* (2006.01)
(Continued)

(52) U.S. Cl.
CPC ............... *H04W 4/80* (2018.02); *A61M 1/74* (2021.05); *A61M 1/96* (2021.05); *G16H 40/20* (2018.01);
(Continued)

(58) Field of Classification Search
None
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Translation of CN104225770A (Year: 2022).*
(Continued)

*Primary Examiner* — Gennadiy Tsvey

(57) ABSTRACT

The present disclosure relates to a network system. The system is formed by at least two negative pressure wound therapy (NPWT) devices. The first NPWT device includes a wireless radio, user interface, controller, and processing circuit. The wireless radio wirelessly communicates with the second NPWT device. The user interface displays operational status of therapy operation, receives a command of operational change from a user, and displays wireless radio connection strength between the first NPWT device and the NPWT device. The controller controls therapy operation of the first NPWT device based on input from the user interface. The processing circuit causes the wireless radio to communicate with the second NPWT device, determines wireless radio connection strength between the first NPWT device and the second NPWT device based on communication between the first NPWT device and the second NPWT device, and causes the user interface to display determined wireless radio connection strength.

14 Claims, 11 Drawing Sheets

(51) Int. Cl.
  *G16H 40/20* (2018.01)
  *G16H 40/60* (2018.01)
  *H04B 17/318* (2015.01)
  *H04W 64/00* (2009.01)
  *H04W 84/18* (2009.01)

(52) U.S. Cl.
  CPC ............ *G16H 40/60* (2018.01); *H04B 17/318* (2015.01); *H04W 64/006* (2013.01); *A61M 2205/18* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/702* (2013.01); *A61M 2205/8206* (2013.01); *H04W 84/18* (2013.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 9,257,028 | B2 * | 2/2016 | Parkulo ............... G08B 25/016 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2007/0258395 | A1 * | 11/2007 | Jollota ................. H04W 72/23 455/67.11 |
| 2009/0154398 | A1 | 6/2009 | Isozu |
| 2010/0022990 | A1 * | 1/2010 | Karpowicz ............ A61M 1/74 604/543 |
| 2011/0092958 | A1 * | 4/2011 | Jacobs .................... A61M 1/95 604/543 |
| 2013/0304006 | A1 * | 11/2013 | Toth ...................... A61M 1/74 604/319 |
| 2014/0030982 | A1 * | 1/2014 | Cardona ................. G01S 5/14 455/67.11 |
| 2014/0149903 | A1 * | 5/2014 | Ahn ..................... G06F 3/0484 715/765 |
| 2015/0099458 | A1 * | 4/2015 | Weisner ............ H04B 7/15507 455/15 |
| 2015/0133829 | A1 * | 5/2015 | DeBusk ................ G16H 20/40 601/6 |
| 2015/0264627 | A1 * | 9/2015 | Perdomo ............... H04W 40/12 370/329 |
| 2016/0184497 | A1 * | 6/2016 | Phillips ................ G16H 20/10 604/319 |
| 2016/0345874 | A1 * | 12/2016 | Raisoni ................ A61B 5/0022 |
| 2017/0105667 | A1 * | 4/2017 | Wei ...................... A61B 5/1112 |
| 2019/0282738 | A1 * | 9/2019 | Hartwell ................. A61M 1/96 |
| 2020/0164120 | A1 * | 5/2020 | Jaecklein ............... A61M 1/90 |
| 2020/0222599 | A1 * | 7/2020 | Gregory ................ G16H 20/40 |

(56) References Cited

U.S. PATENT DOCUMENTS

| | | | |
|---|---|---|---|
| 2020/0352501 A1* | 11/2020 | Hunt | A61B 5/002 |
| 2021/0187171 A1* | 6/2021 | Collinson | A61M 1/962 |

FOREIGN PATENT DOCUMENTS

| | | | | |
|---|---|---|---|---|
| AU | 755496 | B2 | 12/2002 | |
| CA | 2005436 | A1 | 6/1990 | |
| CN | 102805894 | A * | 12/2012 | |
| CN | 104225770 | A * | 12/2014 | A61M 27/00 |
| DE | 26 40 413 | A1 | 3/1978 | |
| DE | 43 06 478 | A1 | 9/1994 | |
| DE | 29 504 378 | U1 | 9/1995 | |
| EP | 0100148 | A1 | 2/1984 | |
| EP | 0117632 | A2 | 9/1984 | |
| EP | 0161865 | A2 | 11/1985 | |
| EP | 0358302 | A2 | 3/1990 | |
| EP | 1018967 | A1 | 7/2000 | |
| GB | 692578 | A | 6/1953 | |
| GB | 2195255 | A | 4/1988 | |
| GB | 2 197 789 | A | 6/1988 | |
| GB | 2 220 357 | A | 1/1990 | |
| GB | 2 235 877 | A | 3/1991 | |
| GB | 2 329 127 | A | 3/1999 | |
| GB | 2 333 965 | A | 8/1999 | |
| JP | 4129536 | B2 | 8/2008 | |
| JP | 2014210020 | A * | 11/2014 | A61B 17/00 |
| KR | 2007038707 | A * | 4/2007 | |
| KR | 2007051516 | A * | 5/2007 | |
| SG | 71559 | | 4/2002 | |
| WO | 80/02182 | A1 | 10/1980 | |
| WO | 87/04626 | A1 | 8/1987 | |
| WO | 90/010424 | A1 | 9/1990 | |
| WO | 93/009727 | A1 | 5/1993 | |
| WO | 94/20041 | A1 | 9/1994 | |
| WO | 96/05873 | A1 | 2/1996 | |
| WO | 97/18007 | A1 | 5/1997 | |
| WO | 99/13793 | A1 | 3/1999 | |
| WO | WO-2013/109410 | A1 | 7/2013 | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
Chariker, Mark E., M.D., et al.; "Effective Management of incisional and cutaneous fistulae with closed suction wound drainage"; Contemporary Surgery, vol. 34, Jun. 1989, pp. 59-63.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A.C. ® Therapy Clinical Guidelines: A Reference Source for Clinicians; Jul. 2007.
International Search Report and Written Opinion in International Application No. PCT/US2019/058485, mailed on Mar. 9, 2020.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

(56) References Cited

OTHER PUBLICATIONS

M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

\* cited by examiner

V.A.C.ULTA™ Therapy System Event Report

| Date | Time | Event |
|---|---|---|
| 03/31/2014 | 09:55 | Patient ID Created |
| | | 12345 |

FIG. 5a

V.A.C.ULTA™ Therapy System Event Report

| Date | Time | Event |
|---|---|---|
| 03/31/2014 | 09:54 | ABTHERA™ Therapy |
| 03/31/2014 | 09:54 | 125 mmHg, Continuous |
| 03/31/2014 | 09:54 | PREVENA™ Therapy |
| 03/31/2014 | 09:54 | 125 mmHg, Continuous |
| 03/31/2014 | 09:54 | V.A.C.® Therapy |
| 03/31/2014 | 09:54 | 125 mmHg, Continuous |
| 03/31/2014 | 09:54 | VERAFLO™ Therapy |
| 03/31/2014 | 09:54 | 125 mmHg, Continuous |
| 03/31/2014 | 09:54 | V.A.C.® Therapy 3.50 hrs |
| 03/29/2014 | 16:43 | Therapy Inactive |
| 03/29/2014 | 16:28 | VERAFLO™ Therapy |
| 03/29/2014 | 16:28 | 125 mmHg, Continuous |
| 03/29/2014 | 16:28 | V.A.C.® Therapy 3.50 hrs |
| 03/29/2014 | 16:23 | VERAFLO™ Therapy |
| 03/29/2014 | 16:23 | 125 mmHg, Continuous |
| 03/29/2014 | 16:23 | V.A.C.® Therapy 3.50 hrs |

FIG. 5b

V.A.C.ULTA™ Therapy System Event Report

| Date | Time | Event |
|---|---|---|
| 03/31/2014 | 09:54 | Therapy Off |
| 03/31/2014 | 09:54 | ABTHERA™ Therapy |
| 03/31/2014 | 09:54 | 125 mmHg, Continuous |
| 03/31/2014 | 09:54 | High Intensity |
| 03/31/2014 | 09:54 | Therapy On |
| 03/31/2014 | 09:54 | Therapy Off |
| 03/31/2014 | 09:54 | PREVENA™ Therapy |
| 03/31/2014 | 09:54 | 125 mmHg, Continuous |
| 03/31/2014 | 09:54 | Low Intensity |
| 03/31/2014 | 09:54 | Therapy On |
| 03/31/2014 | 09:54 | Therapy Off |
| 03/31/2014 | 09:54 | V.A.C.® Therapy |
| 03/31/2014 | 09:54 | 125 mmHg, Continuous |
| 03/31/2014 | 09:54 | Medium Intensity |
| 03/31/2014 | 09:54 | Therapy On |
| 03/31/2014 | 09:54 | Therapy Off |
| 03/31/2014 | 09:54 | VERAFLO™ Therapy |
| 03/31/2014 | 09:54 | 125 mmHg, Continuous |
| 03/31/2014 | 09:54 | V.A.C.® Therapy 3.50 hrs |
| 03/31/2014 | 09:54 | Medium Intensity |
| 03/31/2014 | 09:54 | Soak 3 mins |
| 03/31/2014 | 09:54 | Start V.A.C.® Phase |
| 03/31/2014 | 09:54 | Instill Vol 10 mL |
| 03/31/2014 | 09:54 | Therapy On |
| 03/29/2014 | 16:28 | Therapy Off |
| 03/29/2014 | 16:28 | VERAFLO™ Therapy |
| 03/29/2014 | 16:28 | 125 mmHg, Continuous |
| 03/29/2014 | 16:28 | V.A.C.® Therapy 3.50 hrs |
| 03/29/2014 | 16:28 | Medium Intensity |
| 03/29/2014 | 16:28 | Soak 3 mins |
| 03/29/2014 | 16:28 | Start V.A.C.® Phase |
| 03/29/2014 | 16:28 | Instill Vol 10 mL |
| 03/29/2014 | 16:28 | Therapy On |
| 03/29/2014 | 16:28 | Continue Therapy |
| 03/29/2014 | 16:27 | Power On |
| 03/29/2014 | 16:23 | VERAFLO™ Therapy |
| 03/29/2014 | 16:23 | 125 mmHg, Continuous |
| 03/29/2014 | 16:23 | V.A.C.® Therapy 3.50 hrs |
| 03/29/2014 | 16:23 | Medium Intensity |
| 03/29/2014 | 16:23 | Soak 3 mins |
| 03/29/2014 | 16:23 | Start V.A.C.® Phase |
| 03/29/2014 | 16:23 | Instill Vol 10 mL |
| 03/29/2014 | 16:23 | Therapy On |
| 03/29/2014 | 16:23 | New Patient |

FIG. 5c

SHORT RANGE PEER TO PEER NETWORK FOR NEGATIVE PRESSURE WOUND THERAPY DEVICES

CROSS-REFERENCE TO RELATED APPLICATIONS

This application claims the benefit of priority to U.S. Provisional Application No. 62/753,759, filed on Oct. 31, 2018, which is incorporated herein by reference in its entirety.

BACKGROUND

The present disclosure relates generally to negative pressure wound therapy devices and more particularly to status and device health monitoring of negative pressure wound therapy devices.

SUMMARY

One implementation of the present disclosure relates to a network system for a hospital. The system includes negative pressure wound therapy devices which form a network for the hospital. The negative pressure wound therapy devices include a first negative pressure wound therapy device and a second negative pressure wound therapy device. The first negative pressure wound therapy device includes a wireless radio, a user interface, a controller, and a processing circuit. The wireless radio is configured to wirelessly communicate with the second negative pressure wound therapy device. The user interface is configured to display to a user an operational status of a therapy operation, receive a command of an operational change from the user, and display to the user a wireless radio connection strength between the first negative pressure wound therapy device and the second negative pressure wound therapy device. The controller is configured to control the therapy operation of the first negative pressure wound therapy device based on an input from the user interface. The processing circuit is configured to cause the wireless radio to communicate with the second negative pressure wound therapy device, determine the wireless radio connection strength between the first negative pressure wound therapy device and the second negative pressure wound therapy device based on the communication between the first negative pressure wound therapy device and the second negative pressure wound therapy device, and cause the user interface to display the determined wireless radio connection strength to the user.

In some embodiments, the first negative pressure wound therapy device further includes an energy storage device configured to store energy and to power the first negative pressure wound therapy device using the stored energy.

In some embodiments, the processing circuit is configured to cause the wireless radio to receive information from the second negative pressure wound therapy device. In some embodiments, the information from the second negative pressure wound therapy device includes at least one of an operational status of the second negative pressure wound therapy device, a remaining energy level of an energy storage device of the second negative pressure wound therapy device, an alert regarding at least one of a low remaining energy level of the energy storage device and a malfunction of the second negative pressure wound therapy device, a device identification value of the second negative pressure wound therapy device, a log of wound therapy information of the second negative pressure wound therapy device over a previous time period, and a signal strength between a second wireless network and the second negative pressure wound therapy device.

In some embodiments, the log of wound therapy information of the second negative pressure wound therapy device includes at least one of a negative pressure wound therapy event, a patient, a mode of negative pressure wound therapy, a therapy start time, a therapy end time, a therapy duration, an instillation quantity, a wound size progress, and an intensity of negative pressure wound therapy.

In some embodiments, the processing circuit is configured to cause the user interface to display to the user the information received from the second negative pressure wound therapy device in response to an administrative request from the user.

In some embodiments, the processing circuit is configured to communicate information to an external device through a serial communications interface. In some embodiments the information includes at least one of the information received from the second negative pressure wound therapy device, the operational status of the first negative pressure wound therapy device, and a log of information of the first negative pressure wound therapy device.

In some embodiments, the first negative pressure wound therapy device is further configured to export log information to an external network. In some embodiments the log information includes at least one of the information received from the second negative pressure wound therapy device, the operational status of the first negative pressure wound therapy device, and a log of information of the first negative pressure wound therapy device.

In some embodiments, the external network includes at least one of an external wireless network, a remote database, and a hospital infrastructure network. In some embodiments the first negative pressure wound therapy device is configured to export the log information to the external network via at least one of a cellular dongle and a wired connection.

In some embodiments, the processing circuit is configured to receive, from the user interface, the command of the operational change from the user, and cause the wireless radio to send the command of the operational change to the second negative pressure wound therapy device to change an operational status of the second negative pressure wound therapy device.

In some embodiments, the command of the operational change is a command to transition the second negative pressure wound therapy device between an active therapy state and an inactive therapy state.

In some embodiments, the network for the hospital is a wireless mesh network. In some embodiments, the processing circuit is configured to cause the wireless radio to communicate with the negative pressure wound therapy devices to form the wireless mesh network.

Another implementation of the present disclosure is a method for monitoring negative pressure wound therapy devices via a wireless network. The method includes receiving, via a wireless radio, information regarding the negative pressure wound therapy devices, and displaying, via a user interface, the information regarding the negative pressure wound therapy devices. In some embodiments, the information regarding the negative pressure wound therapy devices includes at least one of an operational status of the each of the negative pressure wound therapy devices, a remaining energy level of an energy storage device of each of the negative pressure wound therapy devices, an alert regarding at least one of a low remaining energy level of the energy storage device and a malfunction of each of the negative pressure wound therapy devices, a device identification value of each of the negative pressure wound therapy devices, a log of operational information of each of the negative pressure wound therapy devices over a previous time period, and a signal strength between a second wireless network and each of the negative pressure wound therapy devices.

In some embodiments, the method includes exporting the information regarding the negative pressure wound therapy devices to an external device through at least one of a serial communications interface and the wireless radio.

In some embodiments, the external device is a personal computer device including a wireless radio configured to communicate with the negative pressure wound therapy devices.

In some embodiments the personal computer device is a smartphone configured to communicate wirelessly with the negative pressure wound therapy devices through an application configured to cause the wireless radio of the smartphone to communicate with the wireless radio of the negative pressure wound therapy devices.

In some embodiments, the external device is configured to send the information regarding the negative pressure wound devices to at least one of a remote database, and a hospital infrastructure network.

In some embodiments, the remote database is an electronic medical records system.

In some embodiments, the method includes exporting the information to an external network via at least one of a cellular dongle and a wired connection. In some embodiments, the external network is at least one of an external wireless network, a remote database, and a hospital infrastructure network.

In some embodiments, the method includes sending a command to one or more of the negative pressure wound therapy devices. In some embodiments the command is a directive to transition the negative pressure wound therapies between an active therapy state and an inactive therapy state.

In some embodiments, the active therapy state includes at least one of negative pressure wound therapy and instillation therapy.

In some embodiments, the inactive therapy state includes changing an associated wound dressing.

Another implementation of the present disclosure is a method for determining a location of a lost negative pressure wound therapy device. The method includes facilitating communication between a first negative pressure wound therapy device at a first location and the lost negative pressure wound therapy device, determining a signal strength between the first negative pressure wound therapy device and the lost negative pressure wound therapy device based on the communication between the first negative pressure wound therapy device and the lost negative pressure wound therapy device, and displaying, to a user, the signal strength between the first negative pressure wound therapy device and the lost negative pressure wound therapy device via a user interface of the first negative pressure wound therapy device.

In some embodiments, the method includes determining a distance between the first negative pressure wound therapy device and the lost negative pressure wound therapy device based on the signal strength between the first negative pressure wound therapy device and the lost negative pressure wound therapy device, and displaying, to the user, the distance between the first negative pressure wound therapy device and the lost negative pressure wound therapy device.

In some embodiments, the method includes facilitating communication between a second negative pressure wound therapy device at a second location and the lost negative pressure wound therapy device and facilitating communication between a third negative pressure wound therapy device at a third location and the lost negative pressure wound therapy device. The method further includes determining signal strength between the second negative pressure wound therapy device and the lost negative pressure wound therapy device based on the communication between the second negative pressure wound therapy device and the lost negative pressure wound therapy device and determining signal strength between the third negative pressure wound therapy device and the lost negative pressure wound therapy device based on the communication between the third negative pressure wound therapy device and the lost negative pressure wound therapy device. The method further includes determining a distance between the second negative pressure wound therapy device and the lost negative pressure wound therapy device based on the signal strength between the second negative pressure wound therapy device and the lost negative pressure wound therapy device, and determining a distance between the third negative pressure wound therapy device and the lost negative pressure wound therapy device based on the signal strength between the third negative pressure wound therapy device and the lost negative pressure wound therapy device. The method further includes determining the location of the lost negative pressure wound therapy device based on the distance between the first negative pressure wound therapy device and the lost negative pressure wound therapy device, the distance between the second negative pressure wound therapy device and the lost negative pressure wound therapy device, and the distance between the third negative pressure wound therapy device and the lost negative pressure wound therapy device.

In some embodiments, the method includes determining a relative location of the lost negative pressure wound therapy device relative to at least one of the first negative pressure wound therapy device, the second negative pressure wound therapy device, and the third negative pressure wound therapy device and displaying the relative location of the lost negative pressure wound therapy device to the user via a user interface of at least one of the first negative pressure wound therapy device, the second negative pressure wound therapy device and the third negative pressure wound therapy device. In some embodiments, the relative location includes a magnitude and direction of the lost negative pressure wound therapy device relative to at least one of the first negative pressure wound therapy device, the second negative pressure wound therapy device and the third negative pressure wound therapy device.

BRIEF DESCRIPTION OF THE DRAWINGS

FIG. 5a is an example of a log event of one of the NPWT devices of FIG. 1, according to an exemplary embodiment.

FIG. 5b is an example of a log event of one of the NPWT devices of FIG. 1, according to an exemplary embodiment.

FIG. 5c is an example of a log event of one of the NPWT devices of FIG. 1, according to an exemplary embodiment.

DETAILED DESCRIPTION

Figure 1:
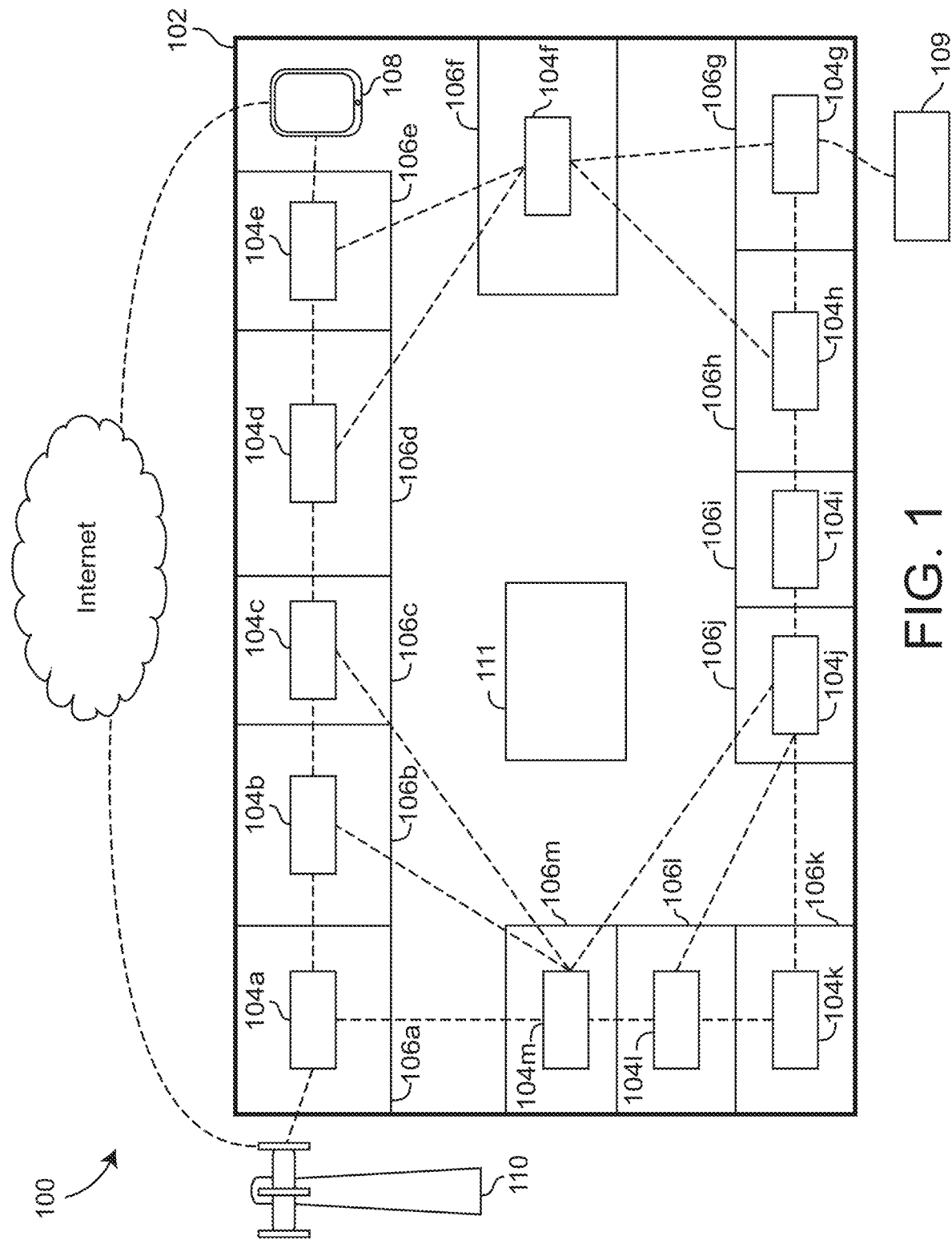
FIG. 1 is a block diagram of a mesh network of negative pressure wound therapy (NPWT) devices in a medical building, according to an exemplary embodiment.

Referring generally to the FIGURES, a mesh network system for negative pressure wound therapy (NPWT) devices in a medical environment (e.g., a hospital) is shown, according to various embodiments. Any of the NPWT devices discussed in the disclosure may be configured to perform NPWT. NPWT is a technique to aid in the healing process of chronic wounds by applying a vacuum to the wound(s). In some cases, fluid (e.g., saline, antibiotics, etc.) may be instilled into the wound(s) and removed through the vacuum. Various foam dressings may be applied to the wound and a film may be placed over the wound, allowing the vacuum to be applied to the wound. Any of the NPWT devices described in the present disclosure may include any pumps, dressings, tanks, reservoirs, etc., necessary to perform NPWT. The devices may be configured to perform any of V.A.C. VeraFlo™ Therapy, Prevena™ Therapy, ABThera™ Therapy, or any other NPWT. The NPWT devices are shown to include controllers configured to wirelessly communicate with each other to form a wireless mesh network. The mesh network may be a Zigbee network and may allow any of the NPWT devices in the mesh network to communicate with each other. The NPWT devices may transmit information, commands, log events, etc., between each other or to other computer devices and/or networks (e.g., a Medical Records System). The mesh network may provide advantages in regards to operation and monitoring of the NPWT devices. The mesh network may also be used to determine approximate locations of lost NPWT devices. The approximate locations of the lost device may be provided to a staff (e.g., a caregiver, a NPWT device operator, etc.) so that the staff can locate the lost NPWT device.

In some cases, the NPWT devices are rotated out of the hospital for servicing when a patient has completed NPWT or rotated into the hospital when a new patient is to begin NPWT. Receiving permission to connect a device to a hospital's wireless network can be a long process. Providing a wireless network between the NPWT devices themselves allows the NPWT devices to be ready for use soon after being rotated into the hospital, and enables the NPWT devices to communicate with each other without being required to be connected to the hospital's wireless network. One or more of the NPWT devices may wirelessly communicate with a cellular tower (as described in greater detail below), and the mesh network formed by the NPWT devices may provide all of the NPWT devices with connection to the cellular tower. Advantageously, if there is a spot of the hospital which does not have cellular coverage, the mesh network can forward data from one of the NPWT devices in the dead spot to a NPWT device with a strong cellular signal. In this way, the mesh network can allow each of the NPWT devices to communicate with the cellular tower and to transmit any information to a remote data center.

In some embodiments, a permanent base unit is connected to the mesh network and is configured to communicably connect with any of the NPWT devices in the mesh network. The permanent base unit may allow a user to monitor and/or control an operation of at least one of the NPWT devices, according to some embodiments. For example, in some embodiments, the user may be able to transition any of all of the NPWT devices into an in-operational state (such that wound dressings can be changed) by sending a command from the permanent base unit to at least one of the NPWT devices. Advantageously, the NPWT devices and the permanent base unit may allow the mesh network to function and operate without needing to connect to the hospital wireless network.

Referring now to FIG. 1, a block diagram of a mesh network 100 is shown, according to an exemplary embodiment. The mesh network 100 is defined by two or more negative pressure wound therapy (NPWT) devices 104. In the exemplary embodiment shown in FIG. 1, the mesh network 100 is defined by NPWT devices 104a-104m. NPWT devices 104a-104m are shown located in rooms 106a-106m of building 102, according to the exemplary embodiment shown. In some embodiments, building 102 is one floor of a hospital or any other medical building. In some embodiments, mesh network 100 is defined by more or less of than the number of NPWT devices 104 shown in FIG. 1. For example, mesh network 100 may be formed by any number of NPWT device 104, according to some embodiments.

NPWT devices 104a-104m are shown communicably connected to each other to form mesh network 100, according to the exemplary embodiment shown. Mesh network 100 may be a communication network such as a Zigbee network, according to an exemplary embodiment. In some embodiments, mesh network 100 may be any other communications network, such as a Wi-Fi network, a Bluetooth network, a LoRa network, and/or any other wireless communications network. According to an exemplary embodiment, the mesh network 100 is an ad-hoc network (i.e., a peer-to-peer network such as a mobile ad hoc network).

As shown in FIG. 1, each of NPWT devices 104a-104m can communicate directly with any of the other NPWT devices 104a-104m, provided that the other NPWT devices 104a-104m are within a wireless communications range. For example, NPWT device 104a (shown located in a far left upper corner of building 102) may be out of range of NPWT device 104g (shown located in a far right bottom corner of building 102) and may not be able to communicate directly with NPWT device 104g. However, the mesh network 100 may provide a communications path between NPWT device 104a and NPWT device 104g. For example, a communications path between NPWT device 104a and NPWT device 104g may be formed by NPWT device 104a, NPWT device 104m, NPWT device 104j, NPWT device 104i, NPWT device 104h, and NPWT device 104g of mesh network 100, allowing NPWT device 104a and NPWT device 104g to communicate with each other.

Each of NPWT devices 104a-104m may communicate with any of the other NPWT devices 104 which form the mesh network 100, according to some embodiments. The NPWT devices 104a-104m may communicate information between each other regarding log events, current status of each of the NPWT devices 104a-104m, control signals, commands, etc. For example, each of the NPWT devices 104a-104m may communicate information regarding an operational status to each of the other NPWT devices 104a-104m. A NPWT device operator (e.g., a caregiver, a nurse, a medical personnel, etc.) may be able to monitor the operational status of the each NPWT devices 104a-104m by viewing a user interface of one of the devices (e.g., NPWT device 104a). The NPWT device operator may view some or all of the information transmitted through mesh network 100. For example, the NPWT device operator may be able to monitor the operational status (i.e., in operation, operation paused, operation started, etc.) of all of NPWT devices 104a-104m which form mesh network 100. In some embodiments, the NPWT device operator is a nurse responsible for the operation of one or more of NWPT devices 104a-104m. The nurse may be stationed in a nurse station, shown as nurse station 111, according to some embodiments. Rather than going to each NPWT device 104a-104m and manually checking a status of each NPWT device 104a-104m, the nurse may go to the nearest NPWT device 104 (e.g., NPWT device 104m) and may monitor the status of all NPWT devices 104a-104m which form mesh network 100 by viewing the user interface of NPWT device 104m. Advantageously, this reduces the need to manually check the status and/or operation of each NPWT device 104a-104m, and allows the nurse the ability to quickly and easily monitor the status/operation of NPWT devices 104a-104m from one of NPWT devices 104a-104m.

In some embodiments, any of the NPWT devices 104a-104m may be configured to send a command to each of the NPWT devices 104a-104m to transition each of the NPWT devices 104a-104m from an active mode to a wound dressing change mode (i.e., an inactive mode). For example, if the NPWT device operator (e.g., the nurse) needs to change wound dressings of each of the NPWT devices 104a-104m, the device operator may go to one of the NPWT devices 104a-104m, and send a command to each of the other NWPT device 104a-104m to transition any or all of the NPWT devices 104a-104m into the wound dressing change mode. In the wound dressing change mode, the operation of one or more of the NPWT devices 104a-104m may pause, allowing the NPWT device operator to change the wound dressings of the paused NPWT devices 104. When the NPWT device operator has finished changing the wound dressings of one or more of the NPWT devices 104a-104m, the NPWT device operator may send a command to transition one or more of the NPWT devices 104a-104m into the active mode from any of the NPWT devices 104a-104m.

Referring still to FIG. 1, mesh network 100 is shown communicably connected to a personal computer device, shown as personal computer device 108, according to an exemplary embodiments. Personal computer device 108 may be any of a laptop, a smartphone, a computer, etc., or any other personal computer device 108 configured to communicably connect with mesh network 100. In some embodiments, personal computer device 108 may only communicably connect with mesh network 100 if personal computer device 108 is configured to communicably connect with mesh network 100 via a communications protocol which mesh network 100 uses (e.g., a Zigbee protocol). Personal computer device 108 may connect to one of the NPWT devices 104a-104m (e.g., NPWT device 104e as shown in FIG. 1) and therein be communicably connected to any of the NPWT devices 104a-104m which form mesh network 100.

Personal computer device 108 may be configured to receive any of the information transmitted between NPWT devices 104a-104m which form mesh network 100, according to some embodiments. In some embodiments, personal computer device 108 may be configured to receive and monitor any of the information transmitted between NPWT devices 104a-104m in a manner similar to the user interface of one of the NPWT devices 104a-104m (described in greater detail below with reference to FIG. 4). Personal computer device 108 is also configured to control an operation of one or more NPWT devices 104a-104m according to some embodiments. For example, personal computer device 108 may send a command to transition one or more of the NPWT devices 104a-104m between an active mode of operation and a wound dressing change mode of operation. In some embodiments, personal computer device 108 sends a command through an application. In some embodiments, personal computer device 108 may only send a command if personal computer device 108 has been verified with the mesh network 100 as an administrative device (e.g., personal computer device 108 must provide a password before being allowed to monitor/control any of the NPWT devices 104 of mesh network 100). Advantageously, this allows a NPWT device operator (e.g., a nurse) to transition one or more or all of the NPWT devices 104a-104m between the active mode of operation and the wound dressing change mode of operation from any location in the building 102 where personal computer device 108 may communicably connect with mesh network 100.

Personal computer device 108 may additionally provide Internet connection to the mesh network 100, according to some embodiments. For example, FIG. 1 shows personal computer device 108 connected to the Internet via a cellular tower 110. Personal computer device 108 may be configured to receive any of the information transmitted through mesh network 100 (e.g., log events, historical operational information, NPWT device status of one or more NPWT devices 104, etc.) and upload the information to a remote database on the Internet. In some embodiments, personal computer device 108 is configured to upload the information received from mesh network 100 to an Electronic Medical Records (EMR) or an Electronic Patient Records (EPR) system.

Referring still to FIG. 1, mesh network 100 is shown communicably connected to an external network, shown as network 109, according to some embodiments. Network 109 may be any external and/or upstream network, such as a hospital network infrastructure. Any of NPWT devices 104a-104m may be configured to communicably connect to network 109, according to some embodiments. In some embodiments, network 109 is an EMR system or an EPR system. Mesh network 100 may be configured to communicably connect with network 109 and transmit information regarding device health, status, historical data, etc., of any of NPWT devices 104a-104m which form mesh network 100, according to some embodiments.

Figure 2:
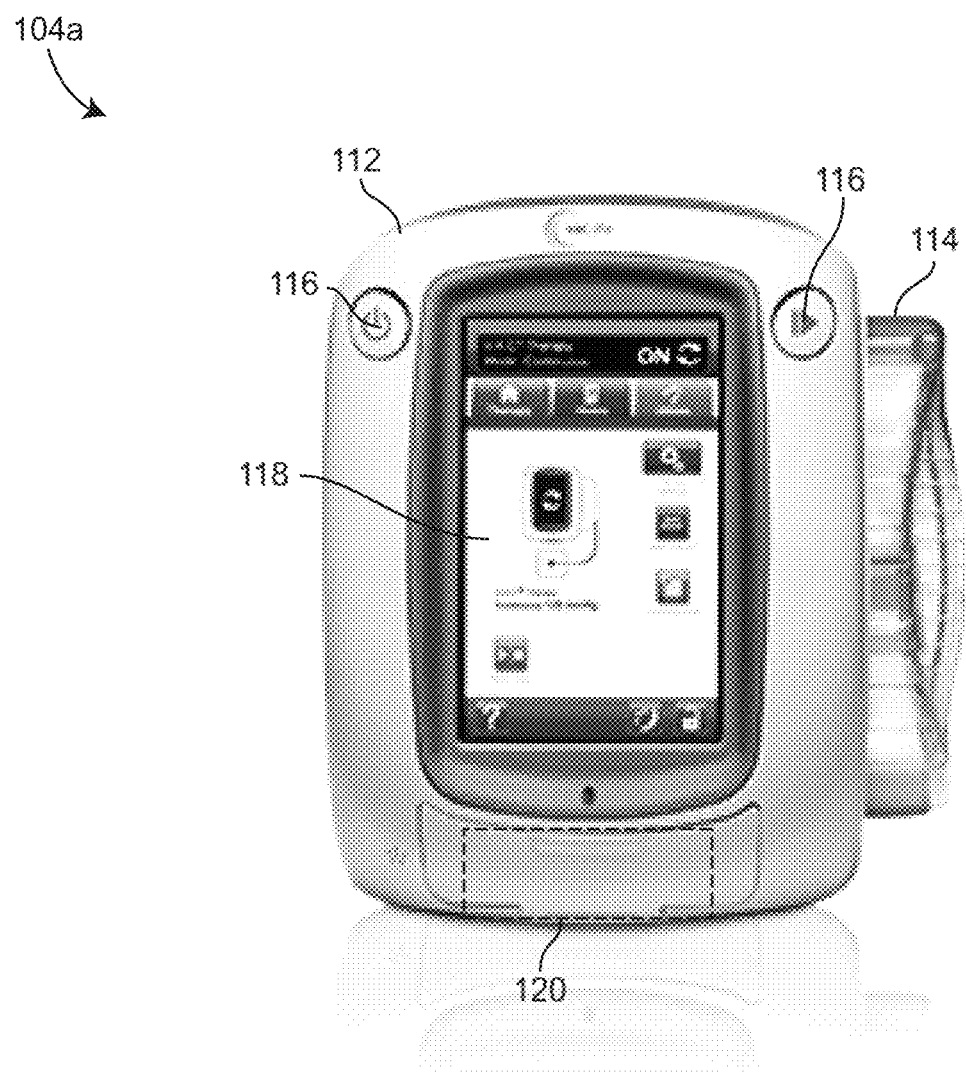
FIG. 2 is a front view of one of the NPWT devices of FIG. 1, shown to include a user interface and a controller, according to an exemplary embodiment.

Referring now to FIG. 2, one of the NPWT devices 104a-104m is shown according to an exemplary embodiment. In FIG. 2, NPWT device 104a is shown, however, each of the NPWT devices 104a-104m may be constructed similarly to NPWT device 104a, such that whatever is said of NPWT device 104a may be said of each of NPWT devices 104a-104m, according to some embodiments. NPWT device 104a is shown to include a housing 112, a canister 114, a user interface 118, and buttons 116 configured to control at least one of an operation of the user interface 118 and a negative pressure operation of NPWT device 104a. NPWT device 104a is also shown to include controller 120 contained within housing 112, according to some embodiments. In some embodiments, NPWT device 104a may be configured to control an operation of a V.A.C. VeraFlo™ Therapy, a Prevena™ Therapy, an ABThera™ Therapy, or any other NPWT. NPWT device 104a may be configured to control an operation of any devices (e.g., a vacuum system, an instillation system, etc.), necessary to complete any of the V.A.C. VeraFlo™ Therapy, Prevena™ Therapy, ABThera™ Therapy, or any other NPWT.

User interface 118 may be configured to display any of the information transmitted through mesh network 100, according to some embodiments. In some embodiments, user interface 118 may display an operational status of NPWT device 104a. For example, user interface 118 may display any of a patient name, a responsible nurse name, a type of NPWT currently being performed by NPWT device 104a, a duration of NPWT, a vacuum pressure of the NPWT, etc., or any other information relevant to the NPWT and/or the mesh network 100. In some embodiments, user interface 118 is any of a resistive touch-screen interface, a surface acoustic wave touch-screen interface, a capacitive touch-screen interface, etc., configured to allow a user to control NPWT device 104a. In some embodiments, user interface 118 is controlled by buttons 116.

Figure 3:
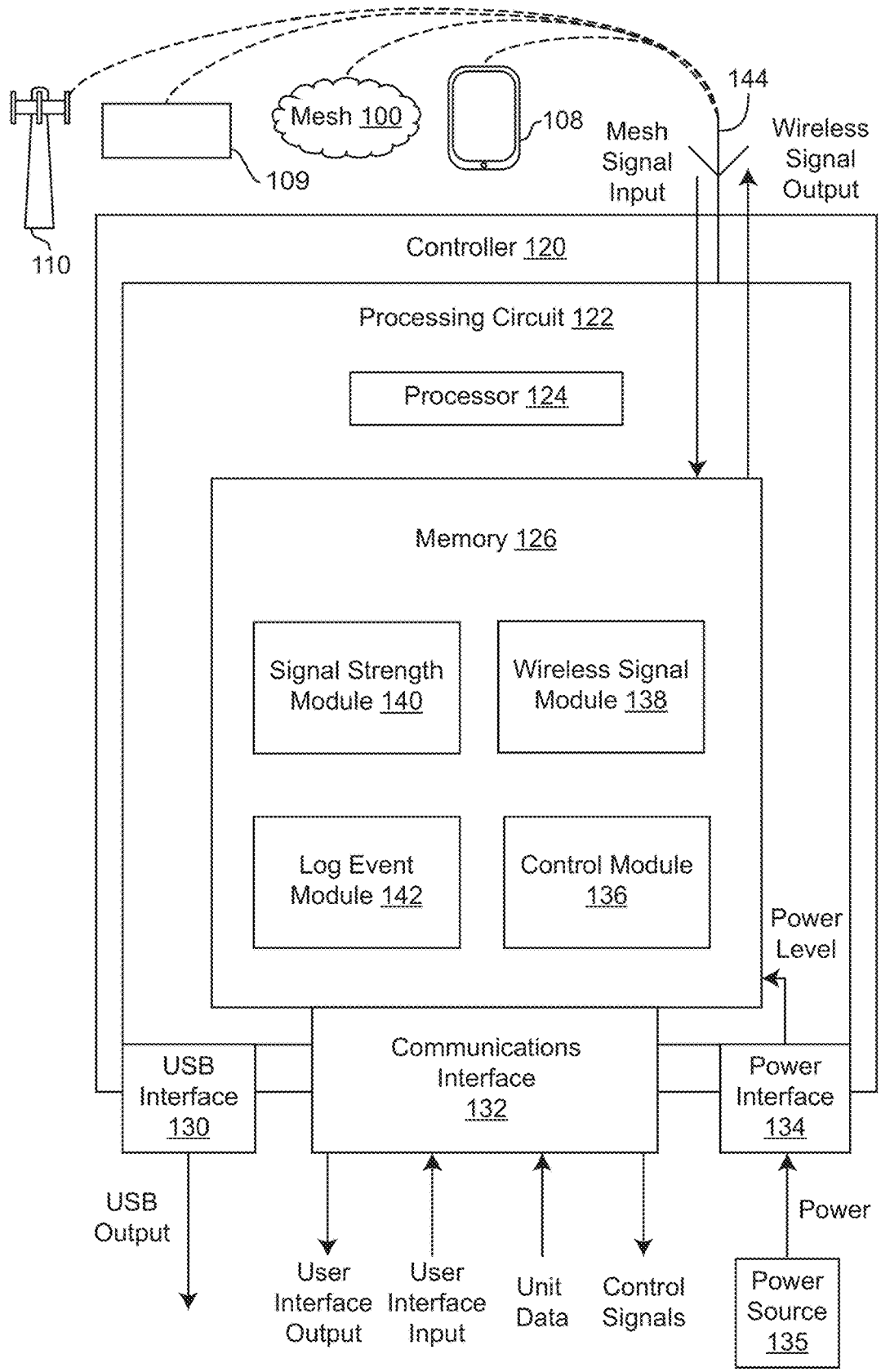
FIG. 3 is a block diagram of the controller of FIG. 2, according to an exemplary embodiment.

Referring now to FIG. 3, a block diagram of controller 120 is shown in greater detail, according to an exemplary embodiment. Controller 120 is shown to include a processing circuit, shown as processing circuit 122. Processing circuit 122 may be configured to perform some or all of the functionality of controller 120, according to some embodiments. Processing circuit 122 is shown to include a processor, shown as processor 124. Processor 124 may be a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Processor 124 may be a microprocessor, or, any conventional processor, controller, microcontroller, or state machine. Processor 124 also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. Processing circuit 122 also include memory, shown as memory 126. Memory 126 (e.g., memory, memory unit, storage device) may include one or more devices (e.g., RAM, ROM, Flash memory, hard disk storage) for storing data and/or computer code for completing or facilitating the various processes, layers and modules described in the present disclosure. Memory 126 may be or include volatile memory or non-volatile memory, and may include database components, object code components, script components, or any other type of information structure for supporting the various activities and information structures described herein. According to an exemplary embodiment, the memory 126 is communicably connected to the processor 124 via processing circuit 122 and includes computer code for executing (e.g., by the processing circuit or the processor) the one or more processes described herein.

Controller 120 is also shown to include a wireless radio, shown as wireless radio 144, according to an exemplary embodiment. Wireless radio 144 may be any kind of wireless transmitter and/or receiver. In some embodiments, wireless radio 144 is a plurality of similar and/or dissimilar wireless radios. Wireless radio 144 may be configured to communicate with one or more wireless radios of one or more controllers of one or more NPWT devices 104. For example, wireless radio 144 may be configured to communicate with any number of NPWT devices 104 which include a controller similar to controller 120, including a wireless radio. Wireless radio 144 is a radio configured to communicate via Zigbee, according to an exemplary embodiment. In other embodiments, wireless radio 144 is configured to communicate via Wi-Fi, Bluetooth, LoRa, a local area network (LAN), a metropolitan area network (MAN), a wide area network (WAN) (e.g., the Internet), ad hoc wireless communications (e.g., MANET), and/or another type of wireless communications. Wireless radio 144 may be configured to communicably connect controller 120 to mesh network 100, and/or personal computer device 108, according to an exemplary embodiment. In some embodiments, wireless radio 144 is a cellular dongle. The cellular dongle may be any cellular dongle that provides controller 120 with an Internet connection or any other upstream network connection (i.e., a connection to cellular tower 110).

Referring still to FIG. 3, controller 120 is shown to include a universal serial bus (USB) interface, shown as USB interface 130, according to an exemplary embodiment. USB interface 130 may be a port for connecting a USB device to controller 120 and allowing controller 120 to serially communicate with the USB device. In some embodiments, USB interface 130 may allow controller 120 to write information to the USB device (e.g., a portable USB device, a hard drive configured to communicate via USB, etc.). In other embodiments, USB interface 130 is any other serial communications interface configured to communicate via SPI (serial peripheral interface), I2C (inter-integrated circuit), USB (universal serial bus), etc., or any other serial communications protocol.

Referring still to FIG. 3, controller 120 is shown to include a communications interface, shown as communications interface 132, according to an exemplary embodiment. Communications interface 132 may be configured to communicably connect controller 120 to at least one of user interface 118, a low level controller configured to control a NPWT operation and monitor an operational status of NPWT device 104a, and one or more devices configured to control and monitor an operational status of negative pressure wound therapy. In some embodiments, communications interface 132 is configured to send control signals to one or more devices configured to control a NPWT operation. Communications interface 132 may be any of a USB interface, an Ethernet interface, a serial peripheral interface (SPI), an inter-integrated circuit interface (I2C), a Recommended Standard 232 (RS-232) interface, etc., or any other serial communications interface. In some embodiments, communications interface 132 is a parallel communications interface. Communications interface 132 may be configured to communicate any or all of the information received from mesh network 100 to user interface 118, according to some embodiments. In some embodiments, communications interface 132 is configured to receive information regarding one or more current operations/statuses of NPWT device 104a (e.g., vacuum pressure, instillation quantity, etc.). Communications interface 132 may receive the information regarding one or more current operations/statuses of NPWT device 104a from at least one of a device configured to perform the NPWT operations, a low level controller configured to control the NPWT operation, user interface 118, etc.

Referring still to FIG. 3, controller 120 is shown to include a power interface, shown as power interface 134, according to an exemplary embodiment. Power interface 134 is configured to draw power supplied by a power source, shown as power source 135, to power controller 120. In some embodiments, power source 135 is any kind of permanent and/or temporary power source. In some embodiments, power source 135 is a battery. In some embodiments, power interface 134 is a connection port for a permanent power source (e.g., AC power and/or DC power) such as a wired 24 VAC connection. In other embodiments, power interface 134 includes both a port for permanent power and/or a power circuit configured to receive and transform power from power source 135. In some embodiments, power interface 134 is configured to receive power from both a permanent power source (e.g., an outlet) and a temporary power source (e.g., a battery). Power interface 134 may include any number of electrical components such as resistors, transistors, capacitors, inductors, diodes, transformers, transistors, switches, diodes, etc., necessary to receive, transform, and supply power to controller 120, according to some embodiments. In some embodiments, if power interface 134 is configured to receive power from a temporary power source (e.g., if power source 135 is a battery), power interface 134 may output power level data of power source 135 to processing circuit 122. The power level data may indicate an amount of energy remaining in power source 135 (e.g., a number of kW-hrs remaining in power source 135).

Referring still to FIG. 3, memory 126 is shown to include various modules, shown as control module 136, wireless signal module 138, signal strength module 140, and log event module 142, according to an exemplary embodiment. Each of these modules is described in greater detail below.

In the embodiment shown in FIG. 3, wireless signal module 138 is shown. Wireless signal module 138 may receive a mesh signal input from mesh network 100 through wireless radio 144. Wireless signal module 138 may be configured to control an operation of wireless radio 144 to output a wireless signal, according to some embodiments. In an exemplary embodiment, wireless signal module 138 includes instructions to control wireless radio 144 to communicate wirelessly via Zigbee. In some embodiments, wireless signal module 138 includes instructions to control wireless radio 144 to communicate wirelessly via Wi-Fi, Bluetooth, LoRa, etc. In some embodiments, the mesh signal input may be encrypted. Wireless signal module 138 may include instructions, methods, keys, etc., for decrypting information received from wireless radio 144. In some embodiments, wireless signal module 138 may also include instructions, methods, keys, etc., for encrypting information sent through wireless radio 144 to mesh network 100. Wireless signal module 138 may receive the mesh signal input, process the mesh signal input, and supply mesh information to any of signal strength module 140, log event module 142, and control module 136. The mesh information may be any of log events of NPWT devices 104a-104m, commands sent from one of NPWT devices 104a-104m, and live operational/status information of any of NPWT devices 104a-104m, according to some embodiments.

Referring still to FIG. 3, controller 120 is shown to include signal strength module 140, according to an exemplary embodiment. Signal strength module 140 may receive the mesh signal input from wireless radio 144, according to some embodiments. In some embodiments, signal strength module may receive the mesh information from wireless signal module 138. Signal strength module 140 is configured to determine a signal strength between NPWT device 104a and any of the other NPWT devices 104b-104m within wireless communications range of NPWT device 104a. In some embodiments, signal strength module 140 is configured to determine the signal strength between NPWT device 104a and each of the NPWT devices 104b-104m which are within wireless communications range of NPWT device 104a. Signal strength module 140 may output the determined signal strengths of each of the NPWT devices 104b-104m within range of NPWT device 104a to user interface 118 through communications interface 132, according to some embodiments.

Signal strength module 140 may also determine a distance associated with the determined signal strength, according to some embodiments. Signal strength module 140 may use any of an equation, a graph, a regression, empirical data, etc., to determine the distance associated with the determined signal strength. The distance associated with the determined signal strength may indicate a distance between NPWT device 104a and one of the other NPWT devices 104b-104m, according to some embodiments. The distance associated with the determined signal strength may be a scalar quantity, or a vector (i.e., having magnitude and direction) in some embodiments. In some embodiments, signal strength module 140 also determines an uncertainty associated with the distance. The uncertainty may be determined based on empirical data in some embodiments. In some embodiments, the uncertainty is a percent uncertainty or a deviation. If the distance associated with the determined signal strength is a scalar quantity, the distance defines a circle having a radius equal to the scalar quantity with the other NPWT device 104 (e.g., NPWT device 104b) being positioned anywhere on the circle.

Referring still to FIG. 3, controller 120 is shown to include log event module 142 according to an exemplary embodiment. Log event module 142 may receive data from any of communications interface 132, power interface 134, control module 136, wireless signal module 138, and wireless radio 144, according to some embodiments. Log event module 142 is configured to determine if a log event has occurred. Log event module 142 is configured to store and/or output the determined log events to at least one of USB interface 130, user interface 118 (through communications interface 132), mesh network 100 (through wireless signal module 138 and wireless radio 144), and control module 136, according to some embodiments. In some embodiments, log event module 142 receives a user interface input through communications interface 132. If the user interface input is a command to change any settings of NPWT device 104a and/or an operation of NPWT device 104a, log event module 142 may determine that a log event has occurred and may output the log event to any of USB interface 130, user interface 118, mesh network 100, and control module 136. In some embodiments, log event module 142 may receive a command from mesh network 100 (through wireless radio 144 and wireless signal module 138) to change an operation or setting of NPWT device 104a. If controller 120 receives a command to change an operation or setting of NPWT device 104a, log event module 142 may determine that a log event has occurred, and may store or output the log event. In some embodiments, log event module 142 may receive a power level signal from power interface 134. If the power level from power interface 134 indicates that the power level of power source 135 has fallen below a lower threshold value, log event module 142 may determine that a log event has occurred and may store or output the log event, according to some embodiments. Log event module 142 may also receive information from communications interface 132 and/or control module 136 regarding an operational status of NPWT device 104a, according to an exemplary embodiment. In some embodiments, log event module 142 is configured to determine if a log event pertaining to the operational status of NPWT device 104a has occurred. For example, if a negative pressure (NP) of the NPWT exceeds a certain threshold value, or deviates from a NP setpoint (e.g., deviates a percentage or a factor of a standard deviation), log event module 142 may determine that a log event has occurred and may store or output the log event.

In some embodiments, log event module 142 may receive log events from any of the other NPWT devices 104b-104m. For example, log event module 142 may receive, through wireless radio 144 and/or wireless signal module 138, a low battery log event for NPWT device 104b. Log event module 142 may store or output any of the log events received from any of the other NPWT devices 104b-104m, according to some embodiments. In some embodiments, log event module 142 outputs the log events to USB interface 130 and/or user interface 118 based on a user interface input received from user interface 118 through communications interface 132. In some embodiments, log event module 142 stores the log events in memory, outputs the log events to another network (e.g., a hospital infrastructure, a medical records system, a personal computer device, etc.) or provides the log events to another NPWT device 104 through wireless radio 144. In some embodiments, log event module 142 may send a request to mesh network 100 to receive any of the log events stored on any of the other NPWT devices 104b-104m. Log event module 142 may cause wireless signal module 138 and/or wireless radio 144 to send the request to mesh network 100. When the log events from mesh network 100 are received, log event module 142 may cause communications interface to send the log events to user interface 118 for viewing by a user. In some embodiments, log event module 142 may output all of the log events received from mesh network 100 to a USB device through USB interface 130. For example, a user may input a command through user interface 118 to output all of the log events of all of NPWT devices 104a-104m over a previous time period to a USB device through USB interface 130. Log event module 142 may cause wireless signal module 138 and/or wireless radio 144 to send a request to all of NPWT devices 104a-104m to transmit any log events which occurred over the previous time period to NPWT device 104a where the user made the request. When all of the log events over the previous time period of all the NWPT devices 104a-104m have been transmitted/received by NPWT device 104a where the user made the request, log event module 142 may output all of the log events over the previous time period to the USB device through USB interface 130. All log events may include a unique identification ID of the particular NPWT device 104 where the log event occurred, as well as a corresponding time and date of the log event. Log events may be any of the log events described in greater detail below with references to FIGS. 5a-5c. Likewise, log event module 142 may be configured to output any log events of any of the NPWT devices 104a-104m to the user interface 118. In some embodiments, log event module 142 may output any of the log events of any of the NPWT devices 104a-104m in response to a user input from user interface 118.

Log event module 142 may also be configured to monitor, categorize, process, receive, and send live operational information of any of the NPWT devices 104a-104m, according to some embodiments. In some embodiments, log event module 142 may receive live operational information from NPWT device 104a through communications interface 132 and/or control module 136. For example, log event module 142 may receive a live NP value from NPWT device 104a through communications interface 132 and/or control module 136, according to some embodiments. Log event module 142 may output the live operational information (e.g., the live NP value) to user interface 118 through communications interface 132, according to some embodiments. In some embodiments, log event module 142 may cause wireless signal module 138 and/or wireless radio 144 to transmit the live operational information of NPWT device 104a to mesh network 100. Log event module 142 may also receive live operation information of any of the other NPWT devices 104b-104m. Likewise, log event module 142 may be configured to cause user interface 118 to display any of the live operational status of any of NPWT devices 104a-104m to a user. In some embodiments, log event module 142 causes user interface 118 to display any of the live operational status of any of NPWT devices 104a-104m to the user in response to a user input request received through user interface 118.

Log event module 142 may also monitor the operational status of NPWT device 104a or the power level received through power interface 134 to determine alarm and/or alert log events. For example, log event module 142 may be configured to determine if a blockage has occurred in the NPWT. Log event module 142 may register the blockage as a log event, and may store the log event, and/or output an alarm/alert to user interface 118 and/or broadcast the alarm/alert to mesh network 100 through wireless radio 144.

Referring still to FIG. 3, controller 120 is shown to include control module 136, according to an exemplary embodiment. Control module 136 may be configured to control and/or control and monitor an operation of NPWT device 104a, according to some embodiments. Control module 136 may determine control signals to adjust an operation of any of the devices used to perform NPWT. For example, control module 136 may generate control signals to control an operation of a vacuum pump, an instillation pump, etc. In some embodiments, control module 136 directly controls any of the devices used to perform NPWT. In some embodiment, control module 136 generates control signals to send to one or more low-level controllers configured to control the operation of any of the devices used to perform NPWT. In some embodiments, control module 136 may receive information from any of the devices used to perform NPWT regarding a live operational status of any of the devices, or may receive information from one or more low-level controllers regarding a live operational status of any of the devices used to perform NPWT. Control module 136 may receive the live operational status of any of the devices used to perform NPWT through communications interface 132, according to some embodiments. In some embodiments, control module 136 may output the control signals to adjust the operation of any of the devices used to perform NPWT through communications interface 132.

In some embodiments, control module 136 may adjust an operation of any of the devices used to perform NPWT based on a command received from user interface 118 and/or received from mesh network 100. For example, control module 136 may receive a command from mesh network 100 to pause operations of all devices used to perform NPWT so that wound dressings can be changed. Control module 136 may receive the command from mesh network 100 through wireless radio 144 and/or wireless signal module 138 and may output a control signal to the devices used to perform NPWT to pause all operations so that the wound dressings can be changed. In some embodiments, control module 136 may receive a command from user interface 118 to pause operations of all devices used to perform NPWT so that wound dressings can be changed. Control module 136 may receive the command from user interface 118 through communications interface 132. In response to the command received from user interface 118, control module 136 outputs a control signal to the devices used to perform NPWT to pause all operations so that the wound dressings can be changed. In some embodiments, the command received from user interface 118 may also include a command to pause operations of all NPWT devices 104a-104m so that wound dressings can be changed for each NPWT device 104a-104m. In some embodiments, control module 136 receives the command from user interface 118, outputs a control signal to pause the devices used to perform NPWT for NPWT device 104a, and additionally causes wireless signal module 138 and/or wireless radio 144 to broadcast a command to mesh network 100 to pause the operation of all NPWT devices 104a-104m.

Referring still to FIG. 3, controller 120 is shown communicably connected via wireless radio 144 to any of cellular tower 110, network 109, mesh network 100, and personal computer device 108, according to some embodiments. Controller 120 may be configured to communicably connect with cellular tower 110 to provide mesh network 100 and all of the NPWT devices 104a-104m with Internet connection, according to some embodiments. In some embodiments, controller 120 communicably connects with network 109. Network 109 may be any of a hospital network infrastructure, a Medical Records System (MRS), or any other external network. Controller 120 may be configured to communicate any of the information received from and/or sent to mesh network 100 to network 109, according to some embodiments.

Figure 4:
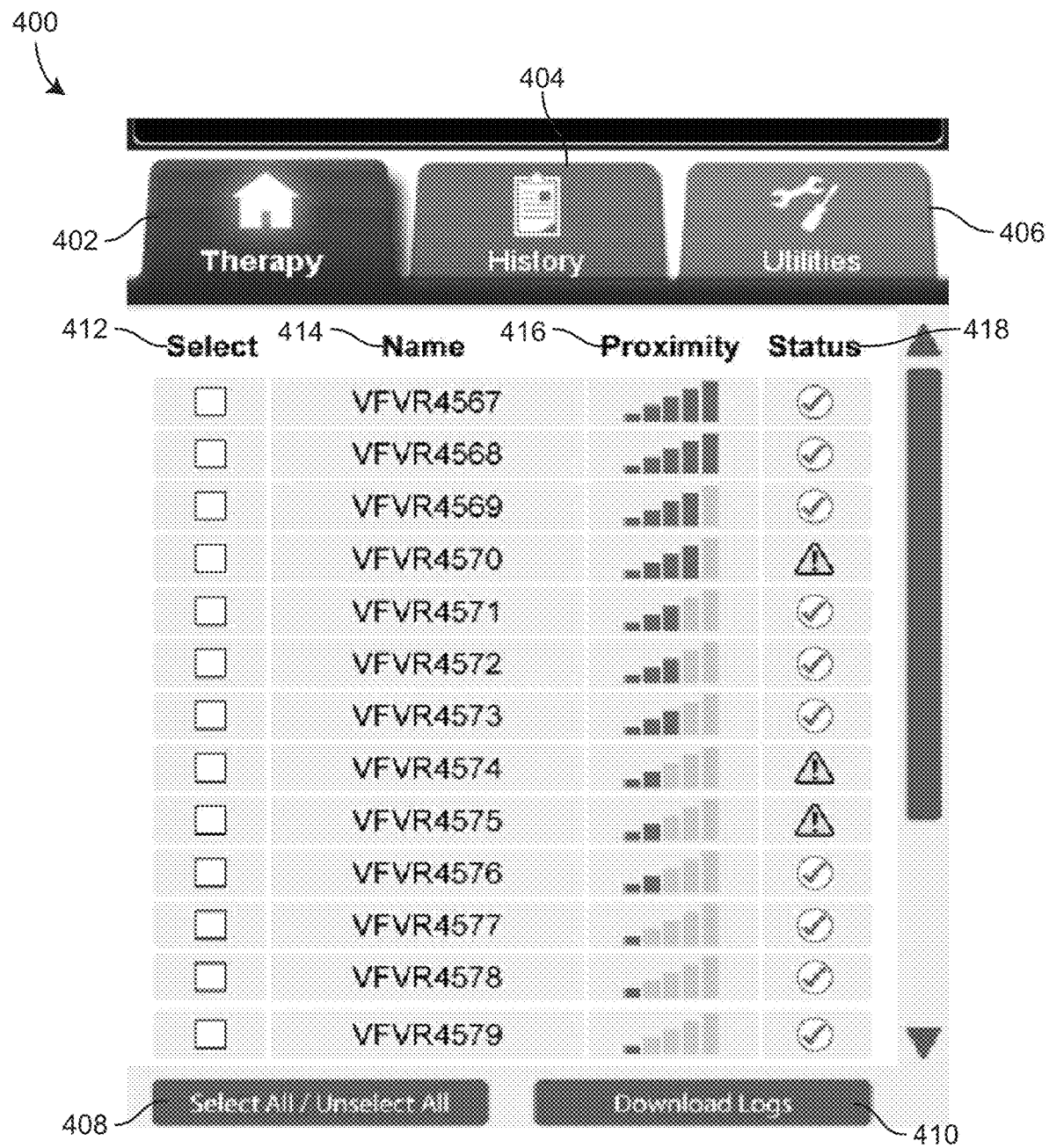
FIG. 4 is an example of the user interface of FIG. 2, according to an illustrative embodiment.

Referring now to FIG. 4, a user interface 400 is shown, according to an exemplary embodiment. The user interface 400 may be an embodiment of user interface 118, according to some embodiments. In some embodiments, user interface 400 is a user interface displayed on personal computer device 108 or displayed on personal computer device 108 through an application. User interface 400 is shown to include a therapy section 402, a history section 404, and a utilities section 406, according to some embodiments. As shown in FIG. 4, the therapy section 402 is selected and shown in greater detail. The therapy section 402 is shown to display information regarding identification names (name column 414) of various NPWT devices 104, proximity (proximity column 416) of the various NPWT devices 104, and status (status column 418) of the various NPWT devices 104, according to some embodiments. In an exemplary embodiment, each of the various NPWT devices 104 which are within communication range of the NWPT device 104 which user interface 400 is displayed on have a unique identification value, shown in the names column 414. The proximity column 416 displays the proximity of each of the various NPWT devices 104 relative to the NPWT device 104 which user interface 400 is displayed on. For example, user interface 400 may correspond to NPWT device 104a of FIG. 1, and each of the NPWT devices 104 shown in the names column 414 may represent various NPWT devices 104 within wireless communications range of NPWT device 104a. In some embodiments, NPWT devices 104 which are outside of direct wireless communications range of NPWT device 104a may be displayed in the therapy section, since NPWT device 104a may still be configured to indirectly wirelessly connect with all of NPWT devices 104a-104m despite not being within direct wireless communications range (e.g., NPWT device 104a can still wirelessly communicate with each of NPWT devices 104b-104m through mesh network 100, despite some of NPWT devices 104b-104m being out of direct wireless communications range with NPWT device 104a).

Referring still to FIG. 4, user interface 400 is shown to include selection column 412, according to some embodiments. Selection column 412 may visually identify which of the various NPWT devices 104 a user has selected. The user may select any (or all) of the NPWT devices 104 by pressing a select button, shown as select button 408 and may download logs from the selected NPWT devices 104 by pressing a download button, shown as download button 410. Download button 410 may send a request to controller 120 of the NPWT device 104 to which user interface 400 is displayed on. Controller 120 may retrieve any of the logs which the user has requested and may display the logs to the user via user interface 400 and/or write the logs to a USB device.

Referring still to FIG. 4, user interface 400 is shown to include status column 418, according to some embodiments. Status column 418 may indicate an operational status of each of the NPWT devices 104, according to some embodiments. In some embodiments, status column 418 may indicate an active or inactive state of NPWT device 104. In some embodiments, status column 418 may indicate an alert of each of NPWT devices 104. For example, status column 418 is shown to include checkmarks and caution symbols. A checkmark may indicate that the corresponding NPWT device 104 is operating properly (e.g., the NPWT device 104 with name VFVR4567 is shown to be operating properly as indicated by a checkmark), according to some embodiments. In some embodiments, the caution symbols may indicate that the corresponding NPWT device 104 is not operating properly (e.g., NPWT device 104 with name VFVR4570 is not operating properly as indicated by a caution symbol). In some embodiments, the caution symbol may indicate that an error has occurred in respect to a NPWT operation of the corresponding NPWT device 104. In some embodiments, the user interface 400 may be configured to display a detailed view of any of the NPWT devices 104 in mesh network 100 to display detailed information of the alarm/alert or the caution symbol.

Referring still to FIG. 4, user interface 400 is shown to include history section 404, according to some embodiments. History section 404 is not shown in detail in FIG. 4, however, history section 404 may display any or all of log events relevant to the NPWT device 104 to which user interface 400 corresponds (i.e., NPWT device 104a). In some embodiments, history section 404 may display any or all of log events related to any or all of the NPWT devices 104 which form mesh network 100 (i.e., NPWT devices 104a-104m). History section 404 may display log information, historical operational information, and graphs of historical information. For example, if some of the log events of one of NPWT devices 104a-104m include data regarding a wound trace area, history section 404 may display a graph of wound trace area versus time.

Referring still to FIG. 4, user interface 400 is shown to include utilities section 406, according to some embodiments. In some embodiments, utilities section 406 may include options to adjust an operation of the NPWT device 104 to which user interface 400 corresponds, and/or to adjust an operation of any of NWPT devices 104a-104m which form mesh network 100. For example, utilities section 406 may display a present operational status of all of NPWT devices 104a-104m which form mesh network 100, and allow a user to select any or all of NPWT devices 104a-104m and send a command to the selected NPWT devices 104 to transition into an inactive therapy state (e.g., pause therapy so that wound dressings can be changed). Conversely, utilities section 406 may allow the user to select any or all of the NPWT devices 104a-104m and send a command to the selected NPWT devices 104 to transition into an active therapy state (resume therapy after wound dressings have been changed) or to change any operational status of NPWT device 104a-104m. Advantageously, this may allow a caregiver to transition any or all of the NPWT devices 104a-104m which form mesh network 100 into an active or inactive therapy state from a single NPWT device 104 (e.g., NWPT device 104a).

In some embodiments, user interface 400 may only be displayed after the NPWT operator (e.g., a nurse, a caregiver, etc.) has logged in and/or provided administrative credentials. The NPWT operator may be required to enter a password or a unique login number to enable administrative features of user interface 400 (administrative features may include any of the features described herein with reference to FIG. 4).

Referring now to FIGS. 5a-5c, log events of one of the NPWT devices 104 is shown, according to an illustrative embodiment. In some embodiments, log events are only created when a setting of one of the NPWT devices 104 is changed, when an operation of one of the NPWT devices 104 changes, or when an alarm/alert is triggered for one of the NPWT devices 104. In some embodiments, the settings are changed manually by a NPWT device operator or by a scheduled operation of the NPWT device 104. Log events may be a database object file that records an event with a corresponding data and time of the recorded event. In some embodiments, log events may be stored as a .log file, a .html file, or a .phi file. FIG. 5a shows a patient ID creation log event, including a corresponding date and time as well as the specific patient ID created, according to an illustrative embodiment. The patient ID creation log event may be generated from a NPWT operator entering a new patient's information through the user interface 118 (or personal computer device 108) of one of the NPWT devices 104a-104m. FIGS. 5b-5c show various log events with corresponding dates and times of one of the NPWT devices 104. FIGS. 5b-5c show log events such as ABTHERA™ Therapy, 125 mmHg, Continuous (i.e., a vacuum pressure), PREVENA™ Therapy, VERAFLO™ Therapy, V.A.C.® Therapy 3.5 hrs, Therapy Inactive, Therapy on, Therapy Off, High Intensity, Low Intensity, Medium Intensity, Soak 3 mins, Start V.A.C.® Phase, Instill Vol 10 mL, Power On, and New patient. Log events may be any events relating to an operational change of the NPWT device 104, a setting change of NPWT device 104, a status change of NPWT device 104, a device health of NPWT device 104, a patient undergoing NPWT from NPWT device 104, a NPWT device operator, etc. Log events may be any of, but not limited to, an operator name (First, Last, Department), a billing patient ID, a power status (Power On, Power Off), a therapy status (Therapy On, Therapy Off, Continue Therapy), a new patient (First Name, Last Name), a therapy type (V.A.C.® Therapy, VERAFLO™ Therapy, PREVENA™ Therapy, ABTHERA™ Therapy), a therapy pressure/mode settings (### Dynamic Pressure Control (DPC) ##/##, ### Continuous, ## mmHg, ## kPa, etc.), intensity (Low Intensity, Medium Intensity, High Intensity), Leak Alarm Threshold Change (V.A.C.® Therapy Leak Threshold 1, V.A.C.® Therapy Leak Threshold 2, V.A.C. VERAFLO™ Leak Threshold 1, V.A.C. VERAFLO™ Leak Threshold 2, PREVENA™ Leak Threshold 1, PREVENA™ Leak Threshold 2, ABTHERA™ Leak Threshold 1, ABTHERA™ Leak Threshold 2, etc.), canister change (Canister Change #), dressing changed, # of foam pieces (Dressing Change #), soak time (Soak # min, Soak # sec), Instill Therapy (Start Instill Phase, Start V.A.C.® Phase), Instill Cassette Changed (VERALINK™ Change), instill fill assist # (Fill Assist Vol ### cc, Fill Assist Vol ### mL), instill volume selected (Instill Vol ### cc, Instill Vol ### mL), settings lock (Settings Locked, Settings Unlocked), screen guard (Screen Guard On, Screen Guard Off), audio pause (Audio Pause On, Audio Pause Off), battery alert (Battery Critical), system fault alert (System Error ########), battery alarm (Battery Critical), therapy inactive alarm/alert (Therapy Inactive), internal temperature alert (Internal Temp), V.A.C.® Therapy blockage alert (NP Block Potential), V.A.C. VeraFlo™ blockage alert (NP Block Potential), PREVENA™ Therapy blockage alert (NP Block Potential), ABThera™ Therapy blockage alert (NP Block Potential), V.A.C.® Therapy low pressure alarm (NP Low Pressure), V.A.C. VeraFlo™ low pressure alarm (NP Low Pressure), V.A.C.® Therapy leak alarm (NP Leak), V.A.C. VeraFlo™ leak alarm (NP Leak), PREVENA™ Therapy leak alert (NP Leak), ABThera™ Therapy leak alert (NP Leak), V.A.C.® Therapy leak alarm—therapy interrupted (NP Leak Off), V.A.C. VeraFlo™ Therapy leak alarm—therapy interrupted (NP Leak Off), V.A.C.® Therapy blockage alarm—therapy interrupted (NP Block), V.A.C. VeraFlo™ Therapy blockage alarm—therapy interrupted (NP Block), PREVENA™ Therapy blockage alert—therapy interrupted (NP Block), ABThera™ Therapy blockage alert—therapy interrupted (NP Block), V.A.C.® Therapy canister full alarm—therapy interrupted (NP Canister Full), V.A.C. VeraFlo™ Therapy canister full alarm—therapy interrupted (NP Canister Full), PREVENA™ Therapy canister full alarm—therapy interrupted (NP Canister Full), ABTHERA™ Therapy canister full alarm—therapy interrupted (NP Canister Full), V.A.C.® Therapy canister not engaged alarm (NP Canister Not Engaged), V.A.C. VeraFlo™ Therapy canister not engaged alarm (NP Canister Not Engaged), PREVENA™ Therapy canister not engaged alarm (NP Canister Not Engaged), ABTHERA™ Therapy canister not engaged alarm (NP Canister Not Engaged), VeraFlo™ Therapy blockage alert (VeraFlo™ Block), VeraFlo™Therapy solution bag/bottle empty alert (Solution Empty), VeraLink™ not engaged alert (VeraLink™ Out), V.A.C. VeraFlo™ Therapy pressure deviation alert (VeraFlo™ Pressure Deviation), PHI password created, PHI access failure, new patient ID created for imaging (Patient ID Created), imaging patient ID, wound image uploaded (Image Uploaded), wound image, patient history note, wound area traced (Area 1 ###.# in², Area 2 ###.# in², Area 3 ###.# in², Area 1 ###.# cm², Area 2 ###.# cm², Area 3 ###.# cm², etc.), wound volume calculated (Vol 1 ###.# in³, Vol 2 ###.# in³, Vol 3 ###.# in³, Vol 1 ###.# cm³, Vol 2 ###.# cm³, Vol 3 ###.# cm³, etc.), date/time change, screen calibration, logs cleared, patient log exported, therapy log exported, alarm log exported, Quality Control (QC) log cleared, QC log exported, language set, entered standard QC, QC complete, entered advanced QC, entered engineering, kernel (operating system) software version, application software version, language version, battery charges reset, battery charges, battery life remaining (battery fuel gauge reading), fuel gauge sync reset, fuel gauge sync days, mains power, battery power, battery charger status (Battery Charger On, Battery Charger Off), instill cassette attachments reset, instill cassette attachments, system hours reset, system hours, therapy hours reset, therapy hours, NP pump hours reset, NP pump hours, pump valve cycles reset, pump valve cycles, wound valve cycles reset, wound valve cycles, instill motor hours reset, instill motor hours, total volume instilled, total volume instilled reset, solution bag/bottle changed (Solution Changed ####), fill assist inactive alert, dressing soak selected, test cycle selected, PIOC version, V.A.C.® Therapy 24-hour summary reset, VeraFlo™ Therapy 24-hour summary reset, Prevena™ Therapy 24-hour summary reset, ABThera™ Therapy 24-hour summary reset, V.A.C.® Therapy accumulated time, VeraFlo™ Therapy accumulated time, VeraFlo™ Therapy accumulated V.A.C.® time, VeraFlo™ Therapy accumulated soak time, VeraFlo™ Therapy accumulated instill volume, VeraFlo™ Therapy accumulated cycles, Prevena™ Therapy accumulated time, ABThera™ Therapy accumulated time, V.A.C.® Therapy accumulated 24-hr time, VeraFlo™ Therapy accumulated 24-hr time, VeraFlo™ Therapy accumulated 24-hr V.A.C.® time, VeraFlo™ Therapy accumulated 24-hr soak time, VeraFlo™ Therapy accumulated 24-hr instill volume, VeraFlo™ Therapy accumulated 24-hr cycles, PREVENA™ Therapy accumulated 24-hr time, and ABThera™ Therapy accumulated 24-hr time.

Figure 6:
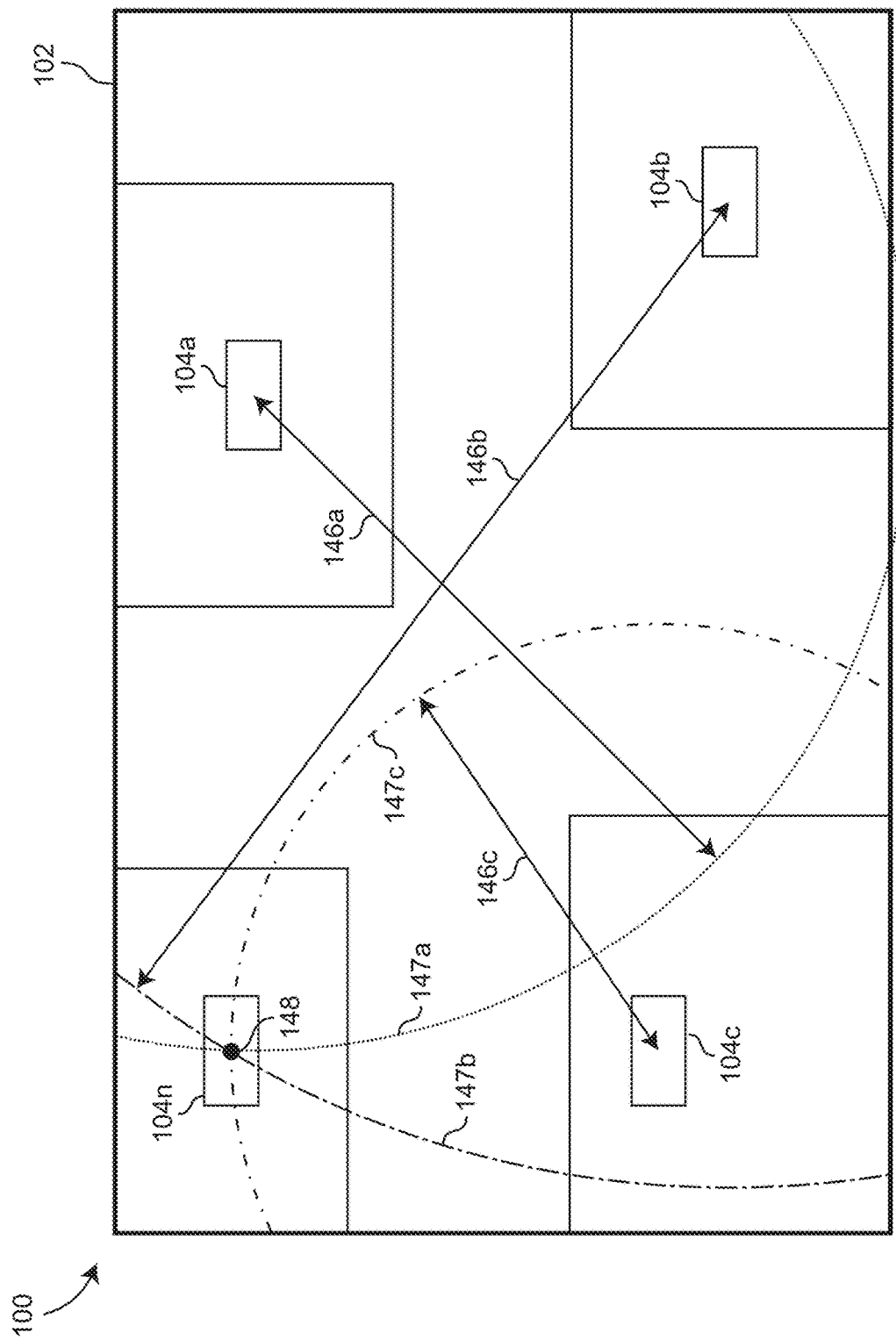
FIG. 6 is a block diagram of a mesh network of negative pressure wound therapy devices, according to an exemplary embodiment.

Referring now to FIG. 6, a block diagram of mesh network 100, according to some embodiments is shown. The embodiment of mesh network 100 shown in FIG. 6 shows mesh network 100 including NPWT device 104a, NPWT device 104b, NPWT device 104c, and NPWT device 104n. NPWT device 104n is a lost NPWT device at an unknown location. NPWT devices 104a-104c are communicably connected to NPWT device 104n, according to some embodiments. Each of NPWT devices 104a-104c may determine a signal strength based on the wireless communications between NPWT devices 104a-104c. Each of NPWT devices 104a-104c may display the signal strength to a user through a user interface. In some embodiments, each of NPWT devices 104a-104c may determine a distance based on the signal strength. For example, NPWT device 104a may establish wireless communications between NPWT device 104a and NPWT device 104n, determine a signal strength between NPWT device 104a and NPWT device 104n based on the wireless communication, and determine a distance 146a between NPWT device 104a and NPWT device 104n based on the signal strength. Each of NPWT device 104b and NPWT device 104c may also determine a signal strength and distance between NPWT device 104b and NPWT device 104n, and NPWT device 104c and NPWT device 104n, respectively. The distance between each of NPWT devices 104a-104c and NPWT device 104n may define circles 147a-147c on which NPWT device 104n may be located. For example, NPWT device 104a is a distance 146a from NPWT device 104n, and the distance 146a defines a circle 147a having a radius equal to distance 146a. In some embodiments, the distances 146a-146c may be useful for locating NPWT device 104n. A caregiver may go to each NPWT device 104a-104c and view the relative distance of NPWT device 104n on a user interface. From a trial and error approach, the caregiver may determine which of NPWT devices 104a-104c NPWT device 104n is closest to. In some embodiments, the caregiver may use a portable personal computer device (e.g., personal computer device 108) to determine an approximate location of NPWT device 104n. The portable personal computer device may communicably connect with NPWT device 104n, and determine a signal strength and distance between the portable personal computer device and NPWT device 104n and display the signal strength and/or distance to the NPWT operator, according to some embodiments. For example, the caregiver may move throughout building 102 along a route, and adjust the route based on the displayed distance and/or signal strength between the portable personal computer device and NPWT device 104n. Any of the signal strength determinations and/or distance determinations described herein with reference to FIG. 9 may be performed by signal strength module 140 according to some embodiments.

In some embodiments, NPWT devices 104a-104n communicate with each other to determine a point of intersection 148 of the three circles 147a-147c. The point of intersection 148 may identify a location of NPWT device 104n relative to any of NPWT device 104a-104c. For example, each of NPWT devices 104a-104c may communicate with each other and determine a distance relative to each other. The NPWT devices 104a-104c may then each communicably connect with NPWT device 104n to determine distances between each of NPWT devices 104a-104c and NPWT device 104n and to define circles 147a-147c, according to some embodiments. The NPWT devices 104a-104c may then determine the location of point of intersection 148 where circles 147a-147c intersect which indicates the position of NPWT device 104n. Each of NPWT devices 104a-104c may then determine a magnitude and direction of NPWT device 104n relative to each of NPWT devices 104a-104c. Each of NPWT devices 104a-104c may then display the magnitude and direction of NPWT device 104n relative to one of NPWT devices 104a-104c to a user via a user interface. In some embodiments, the magnitude and direction may indicate a distance (e.g., 50 feet) and a direction (e.g., North) of NPWT decide 104n relative to one of the NPWT devices 104a-104c.

Figure 7:
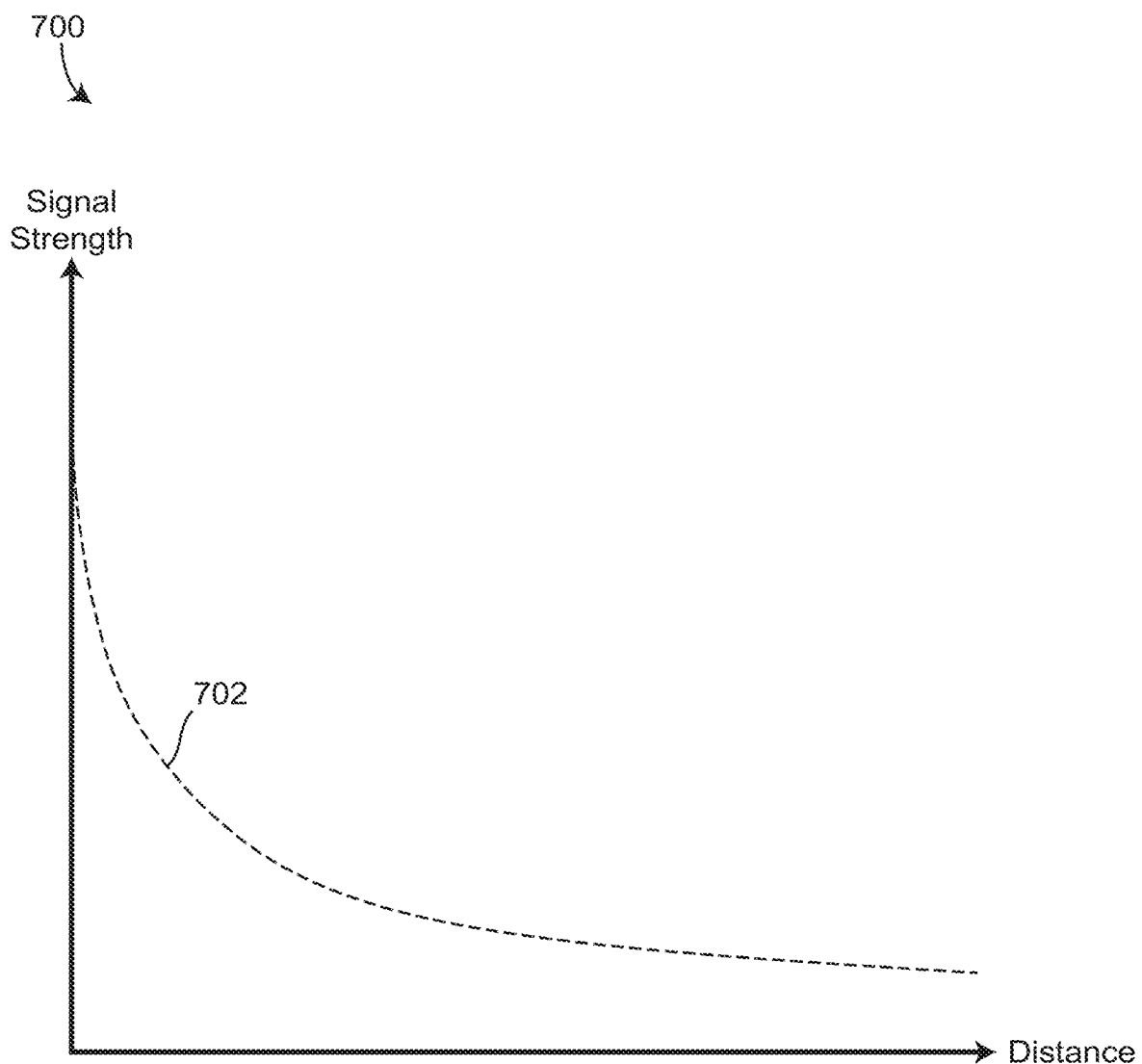
FIG. 7 is a graph of a relationship between signal strength and distance, according to an exemplary embodiment.

Referring now to FIG. 7, a graph 700 of signal strength versus distance is shown, according to some embodiments. Plot 702 of graph 700 shows a trend of signal strength versus distance according to some embodiments. In some embodiments, signal strength module 140 (described in greater detail above with reference to FIG. 3) may use graph 700 to determine a distance based on a signal strength. In some embodiments, signal strength module 140 may use an equation which corresponds to plot 702 to determine the distance based on the signal strength. In some embodiments, signal strength module 140 may use empirical data and a curve fitting algorithm and/or a regression algorithm to determine an equation which represents a relationship between signal strength and distance. In some embodiments, signal strength module 140 may use a lookup table and interpolation techniques to determine a distance based on signal strength.

Figure 8:
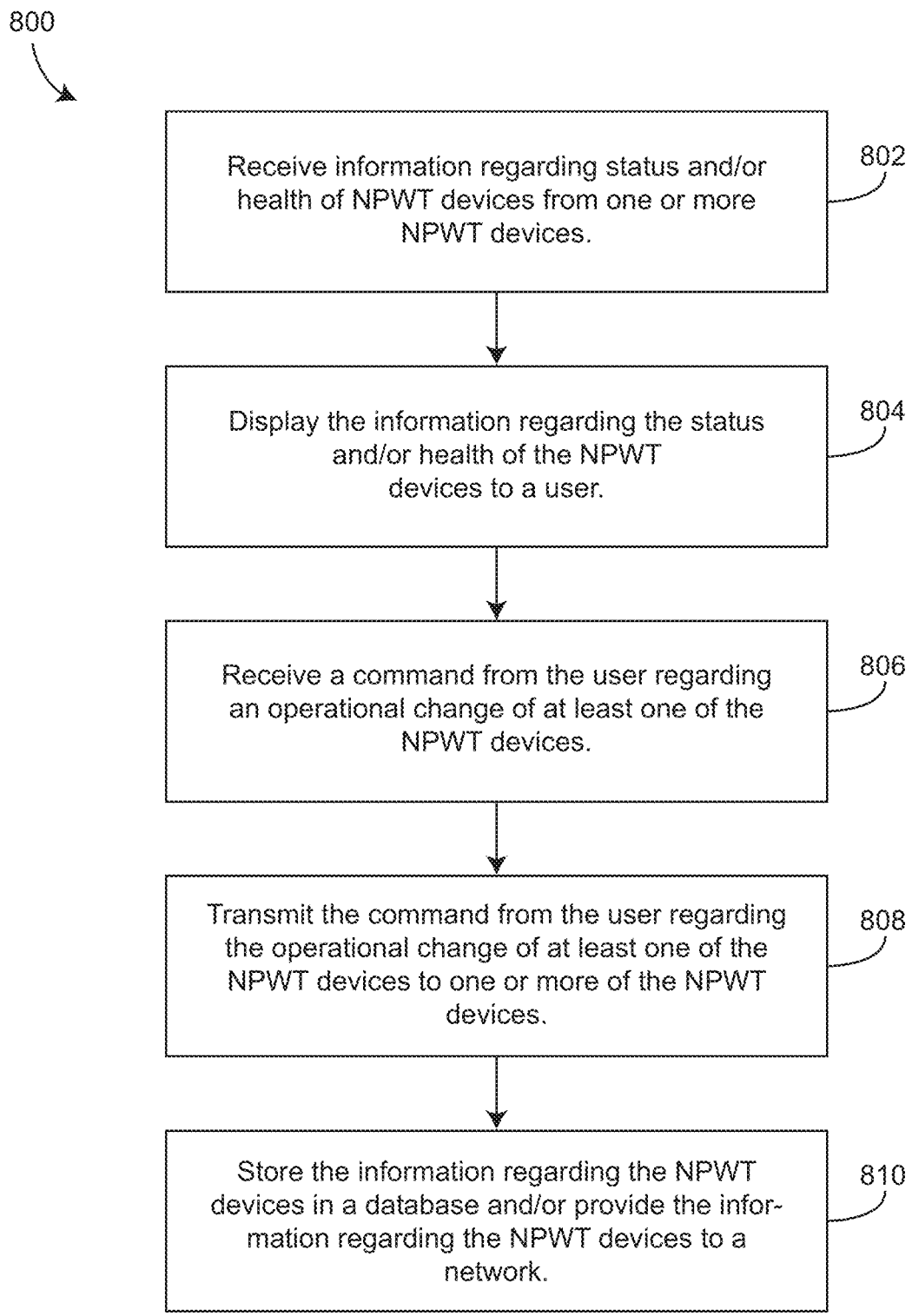
FIG. 8 is a method for transmitting and receiving information between the NPWT devices of FIG. 1, according to an exemplary embodiment.

Referring now to FIG. 8, a method 800 for monitoring the status and/or device health of NPWT devices is shown, according to an exemplary embodiment. Method 800 is shown to include steps 802-810. Step 802 recites receiving information regarding a status and/or health of NPWT devices from one or more NPWT devices. Step 802 may be performed by any NPWT devices which are communicably connected to form a mesh network (e.g., mesh network 100) such as NPWT devices 104a-104m of FIG. 1, according to some embodiments. In some embodiments, the information is received through wireless radio 144 of one of the NPWT devices 104a-104m such as NPWT device 104a. In some embodiments, the information sent from NPWT devices 104b-104m and received by NPWT device 104a is transmitted by a wireless radio 144 of each of NPWT devices 104b-104m. The information transmitted and received may be any of log events of any of the NPWT devices 104a-104m, an operational status of any of the NPWT devices, and an alarm or alert regarding a device health of any of the NPWT devices 104a-104m. In some embodiments, step 802 is facilitated by controller 120 of each of the NPWT devices 104a-104m configured to control an operation of wireless radio 144 of each of the NPWT devices, described in greater detail above with reference to FIG. 3.

Step 804 of method 800 recites displaying the information regarding the status and/or device health of the NPWT devices to a user. Step 804 may be performed by user interface 118 (and/or user interface 400) of one of the NPWT devices 104a-104m and may be facilitated by controller 120 of NPWT device 104a configured to control an operation of the user interface 118. The information displayed to the user may be any of log events of any of the NPWT devices 104a-104m, an operational status of any of the NPWT devices 104a-104m, and an alarm or alert regarding a device health of any of the NPWT devices 104a-104m. In some embodiments, step 804 may be performed in response to a user input from the user interface 118. For example, in some embodiments, step 804 may be only performed after the user has input a request through the user interface 118. The request may be a request to display any or all of the information received from any of the other NPWT devices 104b-104m, according to some embodiments.

Step 806 of method 800 recites receiving a command from the user regarding an operational change of at least one of the NPWT devices 104a-104m. Step 806 may be performed by user interface 118, according to some embodiments. In some embodiments, step 806 may only be performed if the user has administrative credentials. For example, before the user can input a command to change the operational status of at least one of the NPWT devices 104a-104m, the user may be required to enter a password, enter a passcode, enter a user ID with sufficient administrative rights, etc.

Step 808 of method 800 recites transmitting the command from the user regarding the operational change of at least one of the NPWT devices 104a-104m to one or more of the NPWT devices 104a-104m. In some embodiments, step 808 is performed by wireless radio 144 of NPWT device 104a, and facilitated by controller 120. The command from the user regarding the operational change of at least one of the NPWT device 104a-104m may be a command to transition at least one of the NPWT devices 104a-104m from an active therapy state to an inactive therapy state, or to transition at least one of the NPWT devices 104a-104m from an inactive therapy state to an active therapy state. In some embodiments, the command may be received by wireless radio 144 of any of the other NPWT devices 104b-104m and may be processed and implemented by controller 120 of any of the other NPWT devices 104b-104m.

Step 810 of method 800 recites storing the information regarding the NPWT devices 104a-104m in a database and/or providing the information regarding the NPWT devices 104a-104m to a network. In some embodiments, step 810 of method 800 may be performed by controller 120 of one or more of NPWT devices 104a-104m. The information regarding the NPWT devices 104a-104m may be historical log events, according to some embodiments. In some embodiments, the information regarding the NPWT devices 104a-104m may be transmitted to a network. The network may be any of a hospital infrastructure, an EHR system, an EPR system, the Internet, a remote database, or any other network or network device.

Figure 9:
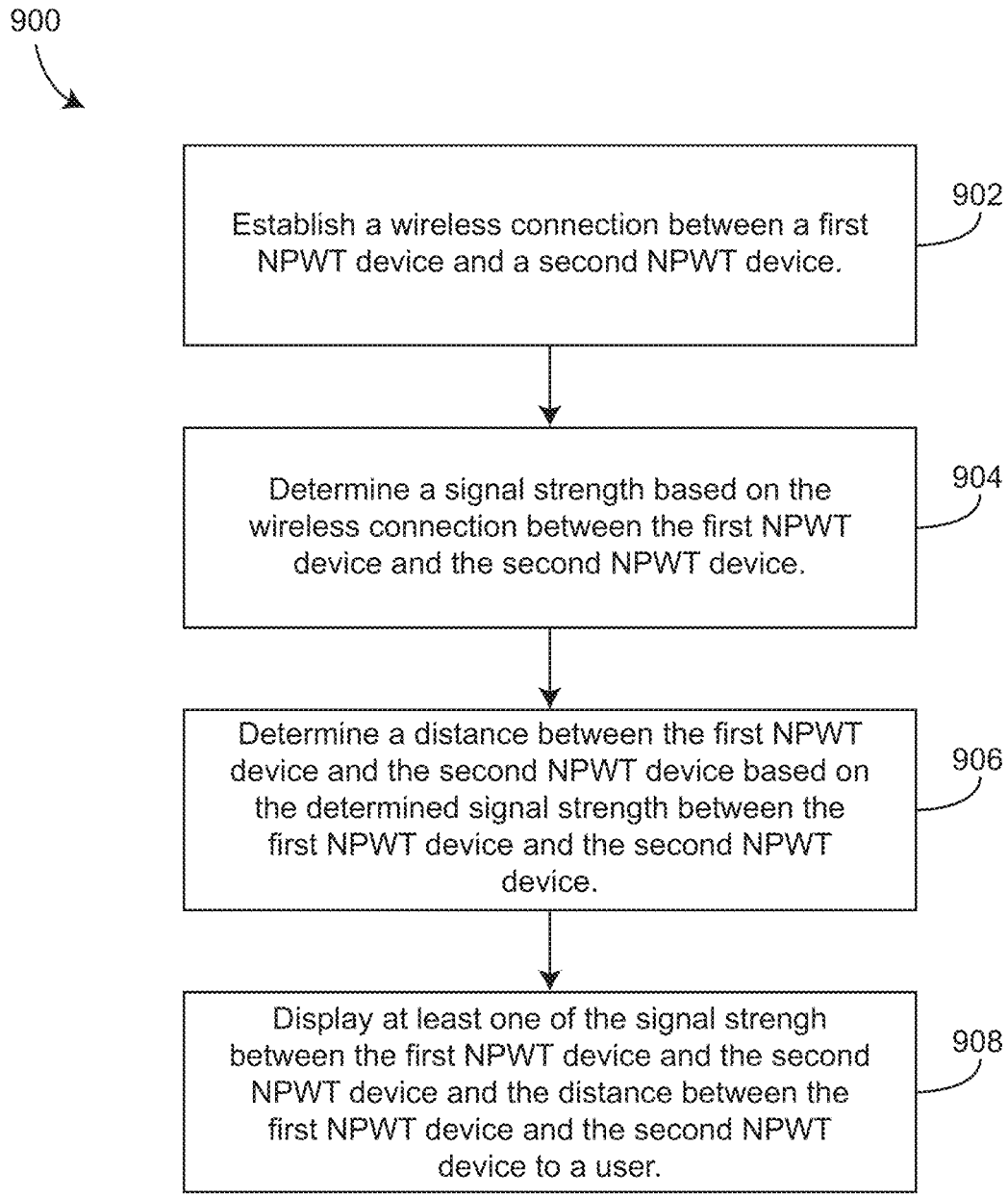
FIG. 9 is a method for determining an unknown location of one of the NPWT devices of FIG. 1, according to an exemplary embodiment.

Referring now to FIG. 9, a method 900 for determining the distance between a first NPWT device and a lost NPWT device is shown, according to some embodiments. Method 900 includes steps 902-908, according to some embodiments. Step 902 of method 900 recites establishing a wireless connection between a first NPWT device and a second (lost) NPWT device. The first NPWT device is NPWT device 104a, according to some embodiments. In some embodiments, the second NPWT device is NPWT device 104n. The wireless connection may be established between the first NPWT device and the second NPWT device by a wireless radio (e.g., wireless radio 144) of each of the first NPWT device and the second NPWT device. In some embodiments, the wireless connection between the first NPWT device and the second NPWT device may be facilitated by a controller (e.g., controller 120) configured to control the wireless radio of each of the first NPWT device and the second NPWT device.

Step 904 of method 900 recites determining a signal strength based on the wireless connection between the first NPWT device and the second NPWT device. In some embodiments, step 904 is performed by controller 120 and signal strength module 140 of the first NPWT device. The signal strength may be indicative of a distance between the first NPWT device (e.g., NPWT device 104a) and the second NPWT device (e.g., NPWT device 104n) in some embodiments.

Step 906 of method 900 recites determining a distance between the first NPWT device (NPWT device 104a) and the second NPWT device (NPWT device 104n) based on the determined signal strength between the first NPWT device and the second NPWT device. Step 906 may be performed by controller 120 and signal strength module 140 of at least one of the first NPWT device and the second NPWT device according to some embodiments. In some embodiments, controller 120 and/or signal strength module 140 of at least one of the first NPWT device and the second NPWT device use any of an equation, a graph (e.g., graph 700 shown in FIG. 7), a look-up table, and empirical data to determine the distance between the first NPWT device and the second NPWT device based on the determined signal strength. In some embodiments, the determined distance between the first NPWT device and the second NPWT device is a scalar quantity and may define a circle having a radius equal to the determined distance.

Step 908 of method 900 recites displaying at least one of the determined signal strength between the first NPWT device and the second NPWT device and the determined distance between the first NPWT device and the second NPWT device to a user. Step 908 may be performed by a user interface (e.g., user interface 118) of one or both of the first NPWT device and the second NPWT device, according to some embodiments. In some embodiments, step 908 is performed by user interface 118 and facilitated by controller 120 configured to control user interface 118.

Figure 10:
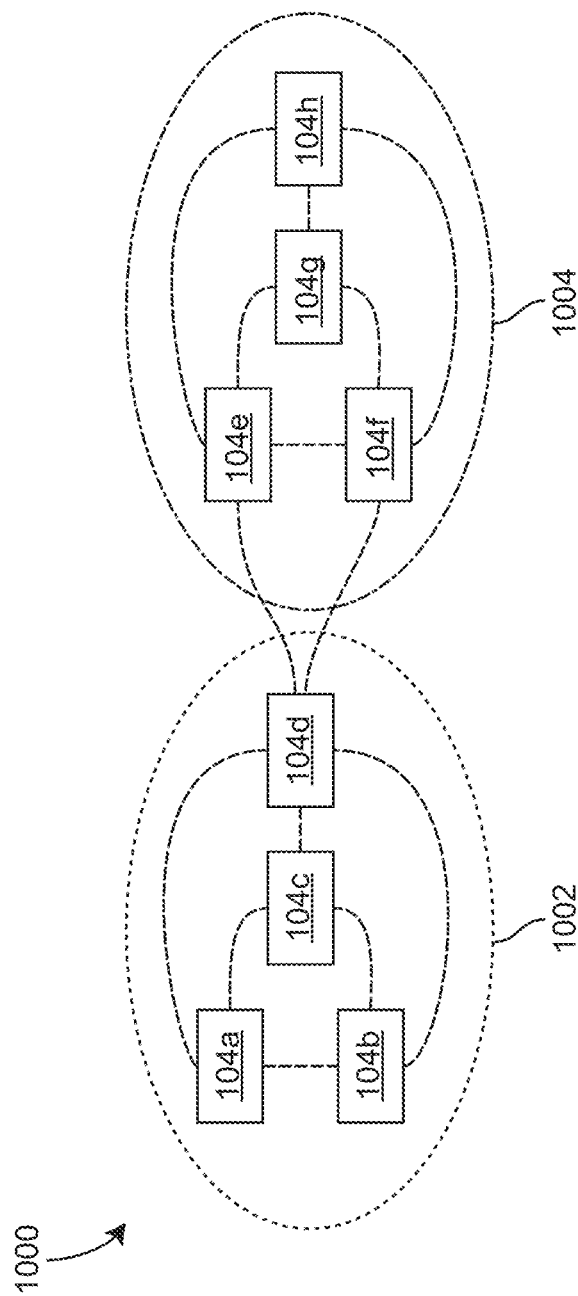
FIG. 10 is a block diagram of a mesh network including a first neighborhood and a second neighborhood of NPWT devices of FIG. 1, according to an exemplary embodiment.

Referring now to FIG. 10, a mesh network 1000 is shown, according to some embodiments. In some embodiments, mesh network 1000 is mesh network 100, as described above in greater detail. In some embodiments, mesh network 1000 is a part of mesh network 100. Mesh network 1000 is shown to include NPWT devices 104a-104h, according to some embodiments. In some embodiments, NPWT devices 104a-104h are configured to wirelessly communicate with each other (as described in greater detail above) to form mesh network 1000. Mesh network 1000 is shown to include a first neighborhood 1002, and a second neighborhood 1004, according to some embodiments. Neighborhood 1002 is shown to include NPWT devices 104a-104d, and neighborhood 1004 is shown to include NPWT devices 104e-104h, according to some embodiments. Each of NPWT devices 104*a*-104*d* which form neighborhood 1002 are shown configured to wirelessly communicate directly with each other to form neighborhood 1002, according to some embodiments. Additionally, each of NPWT devices 104*e*-104*h* are shown configured to wirelessly communicate directly with each other to form neighborhood 1004, according to some embodiments.

Referring still to FIG. 10, neighborhood 1002 and neighborhood 1004 may be configured to communicably connect with each other through direct wireless communication between any of NPWT devices 104*a*-104*d* and NPWT device 104*e*-104*h*, according to some embodiments. For example, as shown in FIG. 10, NPWT device 104*d* is shown wirelessly communicating directly with both NPWT device 104*e* and NPWT device 104*f*, according to some embodiments. In some embodiments, the direct wireless communications between NPWT device 104*d* and NPWT devices 104*e* and 104*f* establishes indirect wireless communications between neighborhood 1002 and neighborhood 1004. For example, NPWT device 104*a* may communicate with any of NPWT devices 104*e*-104*h*, by communicating with NPWT device 104*d*, with NPWT device 104*d* acting as a relay to establish wireless communications between NPWT device 104*a* and any of NPWT devices 104*e*-104*h*, according to some embodiments. Likewise, any of NPWT devices 104*a*-104*d* of neighborhood 1002 may wirelessly communicate with any of NPWT devices 104*e*-104*h* of neighborhood 1004, with NPWT devices 104 able to communicate across neighborhoods 1002-1004 acting as relays, enabling indirect wireless communications.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the mesh network system as shown in the various exemplary embodiments is illustrative only. Additionally, any element disclosed in one embodiment may be incorporated or utilized with any other embodiment disclosed herein. For example, the controller 120 of the exemplary embodiment described in at least paragraph(s) [0050]-[0065] may be incorporated in any of the NPWT devices 104a-104m of the exemplary embodiment described in at least paragraph(s) [0039]-[0047]. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A network system for a hospital, the system comprising:
   a plurality of negative pressure wound therapy devices forming a mesh network for the hospital, wherein the plurality of negative pressure wound therapy devices comprises a first neighborhood including a first set of negative pressure wound therapy devices configured to directly wirelessly communicate with each other to form the first neighborhood and a second neighborhood including a second set of negative pressure wound therapy devices configured to directly wirelessly communicate with each other to form the second neighborhood, at least one of the first neighborhood or the second neighborhood including a first negative pressure wound therapy device and a second negative pressure wound therapy device; and
   an external network configured to communicatively couple with at least one of the plurality of negative pressure wound therapy devices;
   wherein the first negative pressure wound therapy device comprises:
   a wireless radio configured to wirelessly communicate with the second negative pressure wound therapy device;
   a user interface configured to display to a user an operational status of a therapy operation of the first negative pressure wound therapy device, receive a command of an operational change from the user, and display to the user a wireless radio connection strength between the first negative pressure wound therapy device and the second negative pressure wound therapy device;
   a controller configured to control the therapy operation of the first negative pressure wound therapy device based on an input from the user interface; and
   a processing circuit configured to:
   cause the wireless radio to communicate with the second negative pressure wound therapy device and receive live operational information from the second negative pressure wound therapy device, the live operational information including a current negative pressure value of the second negative pressure wound therapy device;
   cause the wireless radio to communicate with the second negative pressure wound therapy device to receive information from the second negative pressure wound therapy device including an alert regarding a malfunction of the second negative pressure wound therapy device;
   determine the wireless radio connection strength between the first negative pressure wound therapy device and the second negative pressure wound therapy device based on the communication between the first negative pressure wound therapy device and the second negative pressure wound therapy device;
   determine a distance between the first negative pressure wound therapy device and the second negative pressure wound therapy device based on the wireless radio connection strength; and
   cause the user interface to display the determined wireless radio connection strength, the distance between the first negative pressure wound therapy device and the second negative pressure wound therapy device, and the live operational information of the second negative pressure wound therapy device to the user.

2. The system of claim 1, wherein at least one negative pressure wound therapy device of the first neighborhood is configured to directly wirelessly communicate with at least one of the negative pressure wound therapy devices of the second neighborhood, and wherein the negative pressure wound therapy devices are configured to act as relays to establish indirect wireless communication between any of the negative pressure wound therapy devices of the first set forming the first neighborhood and any of the negative pressure wound therapy devices of the second set forming the second neighborhood.

3. The system of claim 1, wherein the processing circuit is further configured to cause the wireless radio to receive information from the second negative pressure wound therapy device, wherein the information from the second negative pressure wound therapy device comprises at least one of:
   a remaining energy level of an energy storage device of the second negative pressure wound therapy device;
   an alert regarding a low remaining energy level of the energy storage device;

a device identification value of the second negative pressure wound therapy device;
a log of wound therapy information of the second negative pressure wound therapy device over a previous time period; and
a signal strength between a second wireless network and the second negative pressure wound therapy device.

4. The system of claim 3, wherein the log of wound therapy information of the second negative pressure wound therapy device comprises at least one of:
a negative pressure wound therapy event;
a patient;
a mode of negative pressure wound therapy;
a therapy start time;
a therapy end time;
a therapy duration;
an instillation quantity;
a wound size progress; and
an intensity of negative pressure wound therapy.

5. The system of claim 4, wherein the processing circuit is further configured to cause the user interface to display to the user the information received from the second negative pressure wound therapy device in response to an administrative request from the user.

6. The system of claim 4, wherein the processing circuit is further configured to communicate information to an external device through a serial communications interface, wherein the information comprises at least one of the information received from the second negative pressure wound therapy device, the operational status of the first negative pressure wound therapy device, and a log of information of the first negative pressure wound therapy device.

7. The system of claim 6, wherein the first negative pressure wound therapy device is further configured to export log information to an external network wherein the log information comprises at least one of the information received from the second negative pressure wound therapy device, the operational status of the first negative pressure wound therapy device, and a log of information of the first negative pressure wound therapy device.

8. The system of claim 7, wherein the external network comprises at least one of an external wireless network, a remote database, and a hospital infrastructure network, and wherein the first negative pressure wound therapy device is configured to export the log information to the external network via at least one of a cellular dongle and a wired connection.

9. The system of claim 3, wherein the log of wound therapy information of the second negative pressure wound therapy device comprises a mode of negative pressure wound therapy and at least one of a therapy start time, a therapy end time, and a therapy duration.

10. The system of claim 1, wherein the processing circuit is further configured to:
receive, from the user interface, the command of the operational change from the user; and
cause the wireless radio to send the command of the operational change to the second negative pressure wound therapy device to change an operational status of the second negative pressure wound therapy device.

11. The system of claim 10, wherein the command of the operational change is a command to transition the second negative pressure wound therapy device between an active therapy state and an inactive therapy state.

12. The system of claim 1, wherein the network for the hospital is a wireless mesh network, wherein the processing circuit is configured to cause the wireless radio to communicate with the plurality of negative pressure wound therapy devices to form the wireless mesh network.

13. The system of claim 1, wherein the first set of negative pressure wound therapy devices comprises at least three negative pressure wound therapy devices directly wirelessly coupled to each negative pressure wound therapy device of the first set of negative pressure wound therapy devices and the second set of negative pressure wound therapy devices comprises at least three negative pressure wound therapy devices directly wirelessly coupled to each negative pressure wound therapy device of the second set of negative pressure wound therapy devices.

14. The system of claim 1, wherein the processing circuit is further configured to cause the wireless radio to receive information from the second negative pressure wound therapy device, wherein the information from the second negative pressure wound therapy device comprises a remaining energy level of an energy storage device of the second negative pressure wound therapy device and an alert regarding a low remaining energy level of the energy storage device.

* * * * *